(12) United States Patent
Demko et al.

(10) Patent No.: US 8,263,764 B2
(45) Date of Patent: Sep. 11, 2012

(54) IL-12 MODULATORY COMPOUNDS

(75) Inventors: Zachary Demko, Somerville, MA (US); Lijun Sun, Harvard, MA (US); Howard P. Ng, Belmont, MA (US)

(73) Assignee: Synta Pharmaceuticals Corp., Lexinton, MA (US)

( * ) Notice: Subject to any disclaimer, the term of this patent is extended or adjusted under 35 U.S.C. 154(b) by 0 days.

(21) Appl. No.: 12/978,356

(22) Filed: Dec. 23, 2010

(65) Prior Publication Data

US 2011/0294798 A1 Dec. 1, 2011

Related U.S. Application Data

(62) Division of application No. 11/433,603, filed on May 12, 2006, now Pat. No. 7,863,270.

(60) Provisional application No. 60/680,724, filed on May 13, 2005.

(51) Int. Cl.
*A61K 31/5377* (2006.01)

(52) U.S. Cl. ........ 544/147; 544/278; 544/284; 544/317; 544/350; 546/112

(58) Field of Classification Search ............. 544/317
See application file for complete search history.

*Primary Examiner* — Brian McDowell
(74) *Attorney, Agent, or Firm* — Edwards Wildman Palmer LLP

(57) ABSTRACT

The invention relates to cyclic hydrazone compounds, compositions including the cyclic hydrazone compounds and methods of using and methods of making thereof. The compounds (and compositions) are useful, inter alia, in modulating IL-12 production and processes mediated by IL-12.

3 Claims, No Drawings

IL-12 MODULATORY COMPOUNDS

RELATED APPLICATIONS

This application is a divisional application of U.S. patent application Ser. No. 11/433,603, filed May 12, 2006, allowed, which claims the benefit of U.S. provisional patent application No. 60/680,724, filed May 13, 2005. The entire contents of the afore-mentioned applications are incorporated herein by reference.

BACKGROUND

Interleukin-12 (IL-12) is a heterodimeric cytokine (p70) which plays key roles in immune responses by bridging innate resistance and antigen-specific adaptive immunity. Trinchieri (1993) *Immunol Today* 14:335. For example, it promotes type 1 T helper cell ($T_H1$) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Interleukin-12 (IL-12) is a di-sulfide linked heterodimeric cytokine (p70) composed of two independently regulated subunits, p35 and p40. IL-12 is produced by phagocytic cells and antigen presenting cells, in particular, macrophages and dendritic cells, upon stimulation with bacteria, bacterial products such as lipopolysaccharide (LPS), and intracellular parasites. The well-documented biological functions of IL-12 are induction of interferon-γ expression from T and NK cells and differentiation toward the $T_H1$ T lymphocyte type. IFN-γ, expression of which is induced by IL-12, is a strong and selective enhancer of IL-12 production from monocytes and macrophages. The cytokine IL-23 is a heterodimer composed of a p19 subunit and the same p40 subunit of IL-12. IL-23, similarly to IL-12, is involved in type 1 immune defenses and induces IFN-γ secretion from T cells. IL-27 is formed by the association of EBB, a polypeptide related to the p40 subunit of IL-12, and p28, a protein related to the p35 subunit of IL-12. IL-27 promotes the growth of T cells and is thought to play a role in the differentiation of $T_H1$ cells. Pflanz et al., *Immunity* (2002), 16:779-790.

It has been suggested that, particularly in chronic diseases in which there is ongoing production of IFN-γ, IL-12 production is augmented by IFN-γ. It is presumed that after an infective or inflammatory stimulus that provokes IL-12 production, the powerful feedback loop promotes IL-12- and IL-23-induced IFN-γ to further augment IL-12 production, leading to consequent excessive production of pro-inflammatory cytokines. Furthermore, it has been suggested that IL-27 induces the expression of T-bet, a major $T_H1$-specific transcription factor, and its downstream target IL-12R β2, independently of IFN-γ. In addition, IL-27 suppresses the expression of GATA-3. GATA-3 inhibits $T_H1$ development and causes loss of IL-12 signaling through suppression of IL-12R β2 and Stat4 expression. Lucas et al., *PNAS* (2003), 100: 15047-15052.

IL-12 plays a critical role in multiple-$T_H1$ dominant autoimmune diseases including, but not limited to, multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease. See, for example, Gately et al. (1998) *Annu Rev Immunol.* 16: 495; and Abbas et al. (1996) *Nature* 383: 787.

Inhibiting IL-12 overproduction, or inhibiting the production of cytokines such as IL-23 and IL-27 which promote IL-12 production and/or $T_H1$ development is an approach to treating the just-mentioned diseases. Trembleau et al. (1995) *Immunol. Today* 16: 383; and Adorini et al. (1997) *Chem. Immunol.* 68: 175. For example, overproduction of IL-12 and the resultant excessive $T_H1$ type responses can be suppressed by modulating IL-12, IL-23 and/or IL-27 production. Therefore, compounds that down-regulate IL-12, IL-23 and/or IL-27 production can be used for treating inflammatory diseases. Ma et al. (1998) *Eur Cytokine Netw* 9: 54.

SUMMARY

In one aspect, this invention features compounds of formula (I):

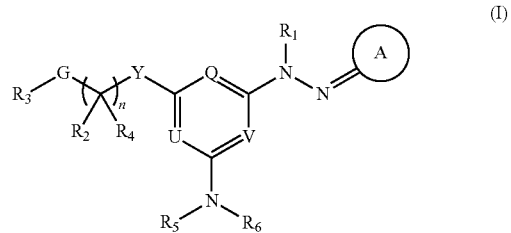

or a pharmaceutically acceptable salt, solvate, clathrate, hydrate, polymorph, or prodrug thereof, wherein:

ring A is an optionally substituted cycloalkyl, an optionally substituted cyclyl, an optionally substituted heterocycloalkyl, or an optionally substituted heterocyclyl, wherein the cycloalkyl, cyclyl, heterocycloalkyl, and heterocyclycl are optionally fused to an optionally substituted cycloalkyl, an optionally substituted cyclyl, an optionally substituted heterocycloalkyl, an optionally substituted heterocyclyl, an optionally substituted aryl, or an optionally substituted heteroaryl;

each of Q, U, and V are independently N or $CR^g$, wherein at least one of Q, U, or V is N; and each $CR^g$ may be the same or different;

Y is a covalent bond, $(CH(R^g))_m$, C(O), C(NR), O, S, S(O), $S(O)_2$, or $NR^k$;

G is a bond, —C(O)$NR^kNR^k$—, —$NR^kNR^kC(O)$—, —$NR^kN$=$CR^k$—, —$CR^k$=$NNR^k$—, —$NR^kNR^k$—, —N(OH)—, —$NR^kO$—, —$ONR^k$—, —C(O)—, —C(NR)—, —$NR^kC(O)$—, —C(O)$NR^k$—, —OC(O)—, —C(O)O—, —OC(O)O—, —$NR^kC(O)O$—, —OC(O)$NR^k$—, —$NR^kC(S)O$—, —OC(S)$NR^k$—, —$NR^k$—C(NR)—$NR^k$—, —$NR^k$—C(O)—$NR^k$—, —$NR^k$—C(S)—$NR^k$—, —$NR^k$—$S(O)_2$—$NR^k$—, —P(O)($R^c$)—, —P(O)($R^c$)O—, —OP(O)($R^c$)—, —OP(O)($R^c$)O—, an optionally substituted cycloalkylene, an optionally substituted cyclylene, an optionally substituted heterocycloalkylene, an optionally substituted heterocyclylene, an optionally substituted arylene, an optionally substituted aralkylene, an optionally substituted heteroarylene, an optionally substituted heteroalkylene, an optionally substituted heteroarylene-NR$^k$—, an optionally substituted heteroarylene-S—, an optionally substituted heteroaralkylene-O—, —Si(OR$^k$)$_2$—, —B(OR$^k$)—, —C(NR)—NR$^k$—, —NR$^k$—CR$^g$R$^g$—C(O)—, —C(O)—ONR$^k$—, —C(O)—NR$^k$O—, —C(S)—ONR$^k$—, —C(S)—NR$^k$O—, —C(NR)—ONR$^k$—, —C(NR)—NR$^k$O—, —OS(O)$_2$—NR$^k$NR$^k$—, —OC(O)—NR$^k$NR$^k$—, —OC(S)—NR$^k$NR$^k$—, —OC(NR)—NR$^k$NR$^k$—, —NR$^k$NR$^k$S(O)$_2$O—, —NR$^k$NR$^k$C(S)O—, —NR$^k$NR$^k$C(NR)O—, —OP(O)(R$^c$)O—, —NR$^k$P(O)(R$^c$)O—, —OP(O)(R$^c$)NR$^k$—, —NR$^k$P(O)(R$^c$)NR$^k$—, —P(O)(R$^c$)NR$^k$—, —NR$^k$P(O)(R$^c$)—, —O-alkylene-heterocycloalkylene-NR$^k$, —NR$^k$—CHR$^g$—C(O)—NR$^k$—CHR$^g$—C(O)—, —NR$^k$—CHR$^g$—C(O)—, —NR$^k$—C(O)—CHR$^g$—, or —C(O)—NR$^k$—CHR$^g$—C(O)—, provided that G is not —NR$^k$N═CR$^k$— or —CR$^k$═NNR$^k$—, when n is 0 and Y is a covalent bond;

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)R$^c$, —OR$^k$, —SR$^k$, —NR$^h$R$^j$, hydroxylalkyl, nitro, cyano, haloalkyl, aminoalkyl, or —S(O)$_2$R$^c$;

R$_1$, for each occurrence, is independently, H or a lower alkyl;

R$_2$ and R$_4$, for each occurrence, are independently, H, an optionally substituted alkyl, an optionally substituted alkylcarbonyl, —OR$^k$, —SR$^k$, —NR$^h$R$^j$, hydroxylalkyl, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or R$_2$ and R$_4$ taken together are ═O, ═S, or ═NR;

R$_3$ is R$^g$;

R$_5$ and R$_6$ are each, independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$_5$ and R$_6$ taken together with the N to which they are attached is an optionally substituted heterocyclyl, an optionally substituted heterocycloalkyl, or an optionally substituted heteroaryl;

R$^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, or mercaptoalkoxy;

R$^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, mercaptoalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, —P(O)R$^c$R$^c$, halo, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the nitrogen to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

m is 0, 1, 2, 3, or 4; and n is 0, 1, 2, 3, 4, 5, 6, or 7.

In another aspect, this invention features compounds of formula (II):

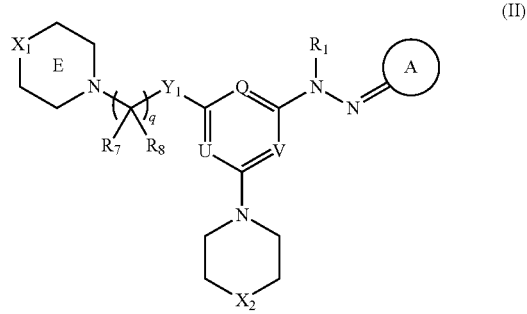

or a pharmaceutically acceptable salt, solvate, clathrate, hydrate, polymorph, or prodrug thereof, wherein:

ring A, Q, U, V, and R$_1$ are defined as for formula (I);

ring E is optionally substituted with one to four substituents selected from a lower alkyl, a halo, an amino, a lower alkyl amino, a lower dialkyl amino, a cyano, a nitro, a lower haloalkyl, a hydroxyl, and a lower hydroxyalkyl;

X$_1$ is O, S, S(O), S(O)$_2$, or CR$^g$R$^g$;

X$_2$ is O, S, S(O), S(O)$_2$, or CH$_2$;

Y$_1$ is O, S, NR$^k$, or CH$_2$;

R$_7$ and R$_8$, for each occurrence, are independently, H or a lower alkyl; or R$_7$ and R$_8$ taken together with the carbon to which they are attached form a cycloalkyl; and q is 0, 1, 2, or 3.

In another aspect, this invention features compounds of formula (III):

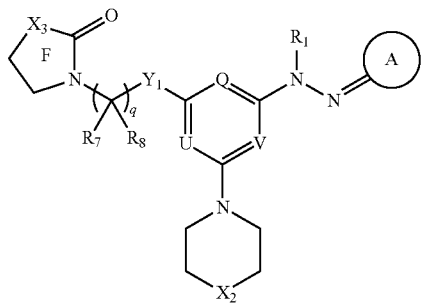

(III)

or a pharmaceutically acceptable salt, solvate, clathrate, hydrate, polymorph, or prodrug thereof, wherein:

ring A, Q, U, V, and R are defined as for formula (I);

$X_2$, $Y_1$, $R_7$, $R_8$ and q are defined as in formula (II);

ring F is optionally substituted with one or two substituents selected from a lower alkyl, a halo, an amino, a lower alkyl amino, a lower dialkyl amino, a cyano, a nitro, a lower haloalkyl, a hydroxyl, and a lower hydroxyalkyl; and $X_3$ is O, $NR^k$, or $CR^gR^g$.

In another aspect, this invention features compounds of formula (IV):

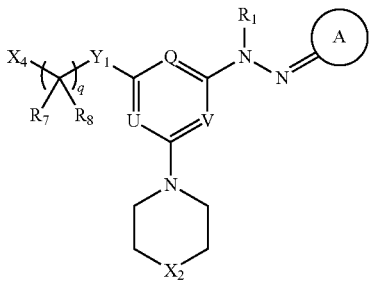

(IV)

or a pharmaceutically acceptable salt, solvate, clathrate, hydrate or polymorph thereof, wherein:

ring A, Q, U, V, and $R_1$ are defined as for formula (I);

$X_2$, $Y_1$, $R_7$, $R_8$ and q are defined as in formula (II); and $X_4$ is —OH, —NH$_2$ or —SH.

In one embodiment, the invention relates to compounds of formula (I), (II), (III), or (IV), wherein one or both of the following provisos apply:

1) when Q, U, and V are all N,

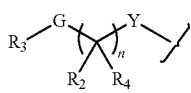

is not a group selected from dimethylamino, diethylamino,

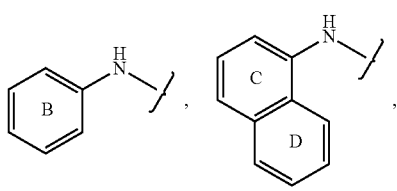

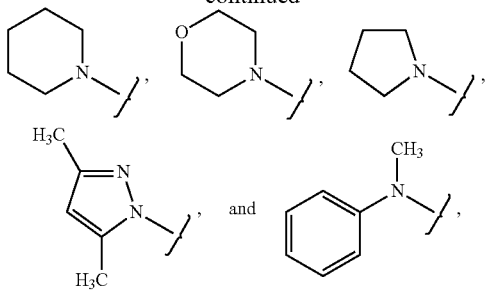

wherein rings B, C, and D are optionally substituted; and 2) when two of U, V, and Q are N and the other is $CR^g$, is not a group selected from a halo, —NH$_2$ or methyl.

In another aspect, this invention features a pharmaceutical composition that includes a pharmaceutically acceptable carrier and at least one compound of this invention (e.g., a compound of formula (I), (II), (III), (IV) or Table 1, or a pharmaceutically acceptable salt, solvate, clathrate, hydrate or polymorph thereof).

In another aspect, the present invention features a method of inhibiting the production of IL-12 and/or inhibiting the production of a cytokine that stimulates or otherwise augments the production of IL-12 (e.g., IL-23 and IL-27) and/or inhibits the proliferation of $T_H1$ lymphocytes in a subject by administering to the subject an effective amount of a compound represented by formula (I), (II), (III), (IV) or Table 1, or a pharmaceutically acceptable salt, solvate, clathrate, hydrate or polymorph thereof.

In another aspect, the invention features a method of inhibiting the production and/or development of $T_H1$ cells in a subject by administering to the subject an effective amount of a compound of formula (I), (II), (III), (IV) or Table 1, or a pharmaceutically acceptable salt, solvate, clathrate, hydrate or polymorph thereof.

In another aspect, the present invention features a method for treating an IL-12 overproduction-related disorder (e.g., multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease). The method includes administering to a subject (e.g., a human or an animal) in need thereof an effective amount of one or more compounds of this invention (including a salt, solvate, clathrate, hydrate, polymorph, or prodrug thereof). The method can also include the step of identifying a subject in need of treatment of diseases or disorders described above. The identification can be in the judgment of a subject or a health professional and can be subjective (e.g., opinion) or objective (e.g., measurable by a test or a diagnostic method).

Also within the scope of this invention are compositions containing one or more compounds of formula (I), (II), (III), (IV) or Table 1, or a pharmaceutically acceptable salt, solvate, clathrate, hydrate or polymorph thereof, for use in treating an IL-12 overproduction-related disorder, and the use of such a composition for the manufacture of a medicament for the just-described use.

Other features, objects, and advantages of the invention will be apparent from the description and from the claims.

DETAILED DESCRIPTION

In one aspect, the invention provides a compound of formula (I):

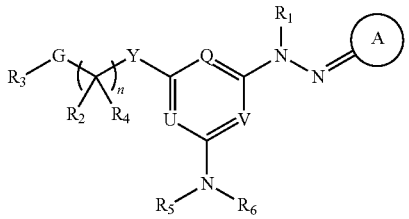

or a pharmaceutically acceptable salt, solvate, clathrate, hydrate, polymorph, or prodrug thereof, wherein:

ring A is an optionally substituted cycloalkyl, an optionally substituted cyclyl, an optionally substituted heterocycloalkyl, or an optionally substituted heterocyclyl, wherein the cycloalkyl, cyclyl, heterocycloalkyl, and heterocyclcl are optionally fused to an optionally substituted cycloalkyl, an optionally substituted cyclyl, an optionally substituted heterocycloalkyl, an optionally substituted heterocyclyl, an optionally substituted aryl, or an optionally substituted heteroaryl;

each of Q, U, and V are independently N or $CR^g$, wherein at least one of Q, U, or V is N; and each $CR^g$ may be the same or different;

Y is a covalent bond, $(CH(R^g))_m$, C(O), C(NR), O, S, S(O), $S(O)_2$, or $NR^k$;

G is a bond, —C(O)$NR^kNR^k$—, —$NR^kNR^kC(O)$—, —$NR^kN$=$CR^k$—, —$CR^k$=$NNR^k$—, —$NR^kNR^k$—, —N(OH)—, —$NR^kO$—, —$ONR^k$—, —C(O)—, —C(NR)—, —$NR^kC(O)$—, —C(O)$NR^k$—, —OC(O)—, —C(O)O—, —OC(O)O—, —$NR^kC(O)O$—, —OC(O)$NR^k$—, —$NR^kC(S)O$—, —OC(S)$NR^k$—, —$NR^k$—C(NR)—$NR^k$—, —$NR^k$—C(O)—$NR^k$—, —$NR^k$—C(S)—$NR^k$—, —$NR^k$—S(O)$_2$—$NR^k$—, —P(O)($R^c$)—, —P(O)($R^c$)O—, —OP(O)($R^c$)—, —OP(O)($R^c$)O—, an optionally substituted cycloalkylene, an optionally substituted cyclylene, an optionally substituted heterocycloalkylene, an optionally substituted heterocyclylene, an optionally substituted arylene, an optionally substituted aralkylene, an optionally substituted heteroarylene, an optionally substituted heteroaralkylene, an optionally substituted heteroarylene-$NR^k$—, an optionally substituted heteroarylene-S—, an optionally substituted heteroaralkylene-O, —Si($OR^k$)$_2$—, —B($OR^k$)—, —C(NR)—$NR^k$—, —$NR^k$—$CR^gR^g$—C(O)—, —C(O)—$ONR^k$—, —C(O)—$NR^kO$—, —C(S)—$ONR^k$—, —C(S)—$NR^kO$—, —C(NR)—$ONR^k$—, —C(NR)—$NR^kO$—, —OS(O)$_2$—$NR^kNR^k$—, —OC(O)—$NR^kNR^k$—, —OC(NR)—$NR^kNR^k$—, —OC(S)—$NR^kNR^k$—, —$NR^kNR^kS(O)_2O$—, —$NR^kNR^kC(S)O$—, —$NR^kNR^kC(NR)O$—, —OP(O)($R^c$)O—, —$NR^kP(O)(R^c)$O—, —OP(O)($R^c$)$NR^k$—, —$NR^kP(O)(R^c)NR^k$—, —P(O) ($R^c$)$NR^k$—, —$NR^kP(O)(R^c)$—, —O-alkylene-heterocycloalkylene-$NR^k$—, —$NR^k$—$CHR^g$—C(O)—$NR^k$—$CHR^g$—C(O)—, —$NR^k$—$CHR^g$—C(O)—, —$NR^k$—C(O)—$CHR^g$—, or —C(O)—$NR^k$—$CHR^g$—C(O)—, provided that G is not —$NR^kN$=$CR^k$— or —$CR^k$=$NNR^k$—, when n is 0 and Y is a covalent bond;

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)$R^c$, —$OR^k$, —$SR^k$, —$NR^hR^j$, hydroxylalkyl, nitro, cyano, haloalkyl, aminoalkyl, or —S(O)$_2R^c$;

$R_1$, for each occurrence, is independently, H or a lower alkyl;

$R_2$ and $R_4$, for each occurrence, are independently, H, an optionally substituted alkyl, an optionally substituted alkylcarbonyl, —$OR^k$, —$SR^k$, —$NR^hR^j$, hydroxylalkyl, —C(O)$R^c$, —OC(O)$R^c$, —SC(O)$R^c$, —$NR^kC(O)R^c$, —C(S)$R^c$, —OC(S)$R^c$, —SC(S)$R^c$, —$NR^kC(S)R^c$, —C(NR)$R^c$, —OC(NR)$R^c$, —SC(NR)$R^c$, —$NR^kC(NR)R^c$, —SO$_2R^c$, —S(O)$R^c$, —$NR^kSO_2R^c$, —OS(O)$_2R^c$, —OP(O)$R^cR^c$, —P(O)$R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R_3$ is $R^g$;

$R_5$ and $R_6$ are each, independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R_5$ and $R_6$ taken together with the N to which they are attached is an optionally substituted heterocyclyl, an optionally substituted heterocycloalkyl, or an optionally substituted heteroaryl;

$R^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, or mercaptoalkoxy;

$R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, mercaptoalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, —P(O)R$^c$R$^c$, halo, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the nitrogen to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

m is 0, 1, 2, 3, or 4; and n is 0, 1, 2, 3, 4, 5, 6, or 7.

In another aspect, this invention features compounds of formula (II):

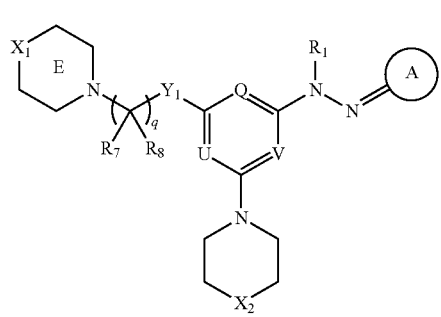

(II)

or a pharmaceutically acceptable salt, solvate, clathrate, hydrate, polymorph, or prodrug thereof, wherein:

ring A, Q, U, V, and R$_1$ are defined as for formula (I);

ring E is optionally substituted with one to four substituents selected from a lower alkyl, a halo, an amino, a lower alkyl amino, a lower dialkyl amino, a cyano, a nitro, a lower haloalkyl, a hydroxyl, and a lower hydroxyalkyl;

X$_1$ is O, S, S(O), S(O)$_2$, or CR$^g$R$^g$;

X$_2$ is O, S, S(O), S(O)$_2$, or CH$_2$;

Y$_1$ is O, S, NR$^k$, or CH$_2$;

R$_7$ and R$_8$, for each occurrence, are independently, H or a lower alkyl; or R$_7$ and R$_8$ taken together with the carbon to which they are attached form a cycloalkyl; and q is 0, 1, 2, or 3.

In another aspect, this invention features compounds of formula (III):

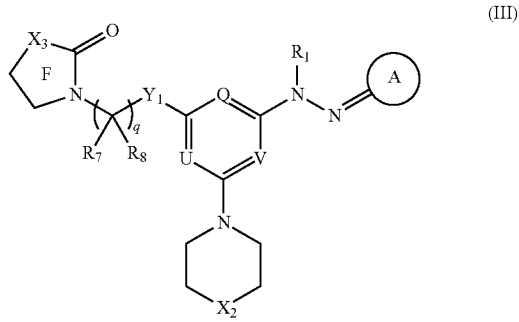

(III)

or a pharmaceutically acceptable salt, solvate, clathrate, hydrate, polymorph, or prodrug thereof, wherein:

ring A, Q, U, V, and R$_1$ are defined as for formula (I);

X$_2$, Y$_1$, R$_7$, R$_8$ and q are defined as in formula (II);

ring F is optionally substituted with one or two substituents selected from a lower alkyl, a halo, an amino, a lower alkyl amino, a lower dialkyl amino, a cyano, a nitro, a lower haloalkyl, a hydroxyl, and a lower hydroxyalkyl; and X$_3$ is O, NR$^k$, or CR$^g$R$^g$.

In another aspect, this invention features compounds of formula (IV):

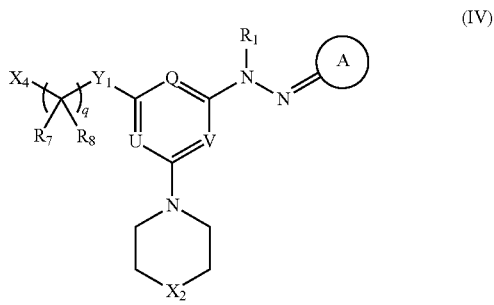

(IV)

or a pharmaceutically acceptable salt, solvate, clathrate, hydrate or polymorph thereof, wherein:

ring A, Q, U, V, and R$_1$ are defined as for formula (I);

X$_2$, Y$_1$, R$_7$, R$_8$ and q are defined as in formula (II); and

X$_4$ is —OH, —NH$_2$ or —SH.

In some embodiments, the invention relates to compounds of formula (I), (II), (III), or (IV), wherein one or both of the following provisos apply:

1) when Q, U, and V are N,

is not a group selected from dimethylamino, diethylamino,

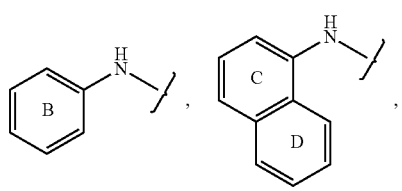

-continued

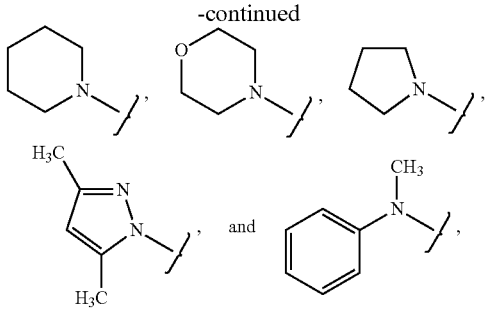

wherein rings B, C, and D are optionally substituted; and
2) when two of U, V, and Q are N and the other is CR$^g$,

is not a group selected from a halo, —NH$_2$ or methyl.

In some embodiments, the invention relates to compounds of formula (I), (II), (III), or (IV), wherein Q, U, and V are N.

In some embodiments, the invention relates to compounds of formula (I), (II), (III), or (IV), wherein one of Q, U, or V is CR$^g$, and the other two are N.

In some embodiments, the invention relates to compounds of formula (I), (II), (III), or (IV), wherein V is CR$^g$, Q and U are N.

In some embodiments, the invention relates to compounds of formula (I), (II), (III), or (IV), wherein Q is CR$^g$, V and U are N.

In some embodiments, the invention relates to compounds of formula (I), (II), (III), or (IV), wherein U is CR$^g$, V and Q are N.

In some embodiments, the invention relates to compounds of formula (I), (II), (III), or (IV), wherein one of Q, U, or V is N, and the other two are CR$^g$.

In some embodiments, the invention relates to compounds of formula (I), (II), (III), or (IV), wherein V is N, and Q and U are CR$^g$.

In some embodiments, the invention relates to compounds of formula (I), (II), (III), or (IV), Q is N, and V and U are CR$^g$.

In some embodiments, the invention relates to compounds of formula (I), (II), (III), or (IV), wherein U is N and Q, and V are CR$^g$.

In some embodiments, the invention relates to compounds of formula (I), wherein —NR$_5$R$_6$ is an optionally substituted morpholino, an optionally substituted thiomorpholino, an optionally substituted 1-oxo-thiomorpholino, an optionally substituted 1,1-dioxo-thiomorpholino, an optionally substituted piperidinyl, or an optionally substituted piperazinyl.

In some embodiments, the invention relates to compounds of formula (I), (II), (III), or (IV), wherein ring A is a ring system selected from the group consisting of:

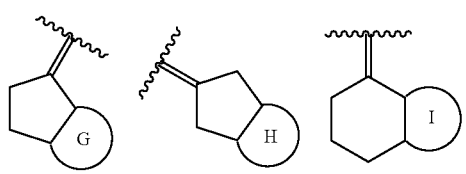

wherein:

"$\xi$"

represents the point of attachment;

rings G, H, I, and J are each, independently, an aryl or a heteroaryl; and each ring system is optionally substituted with one or more substituents.

In some embodiments, the invention relates to compounds of formula (I), (II), (III), or (IV), wherein ring A is a ring system selected from the group consisting of:

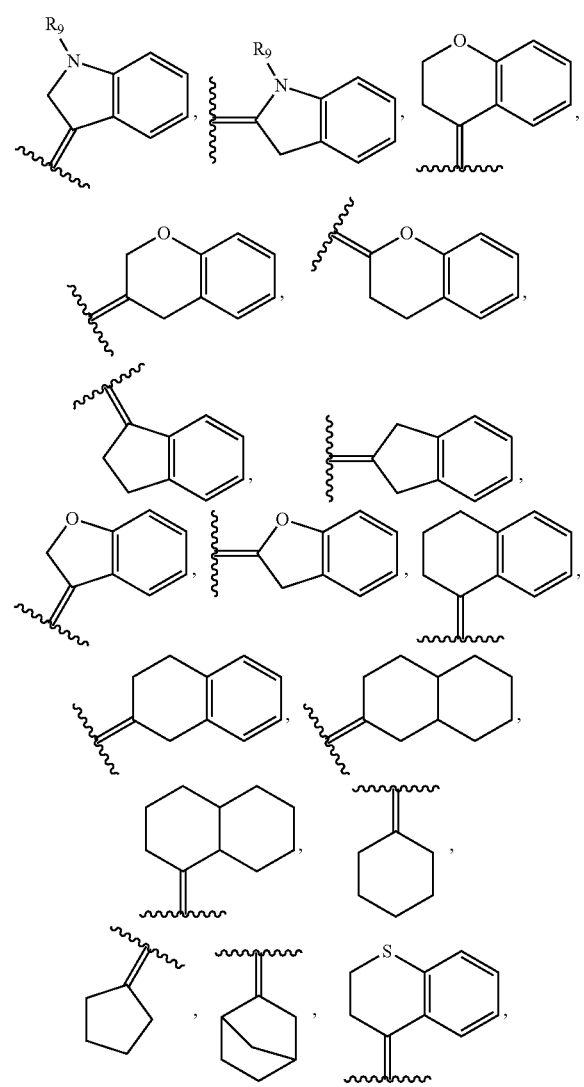

-continued
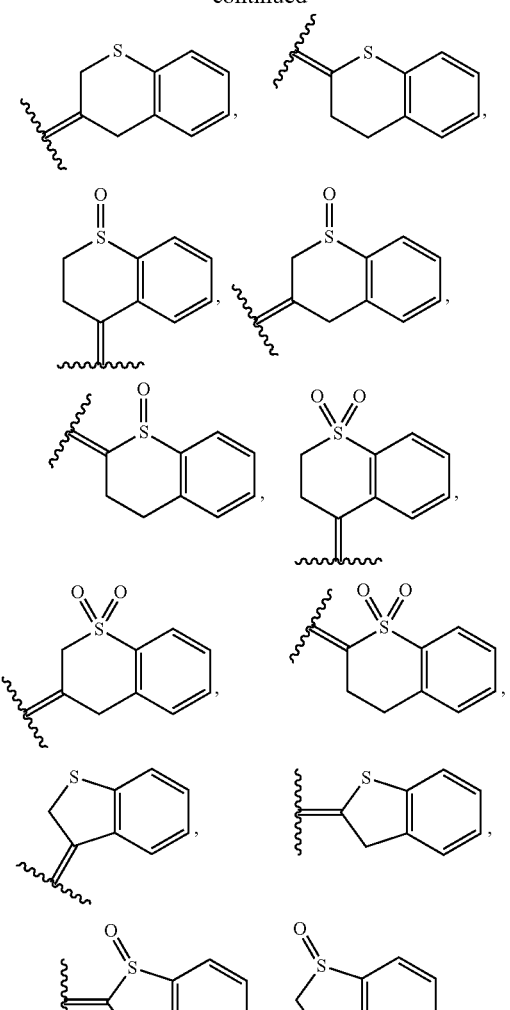
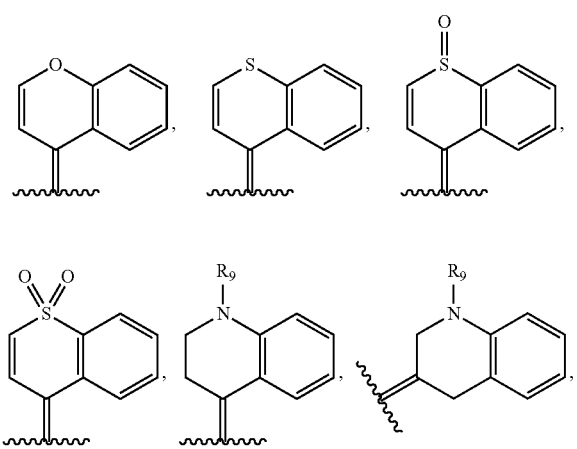
-continued
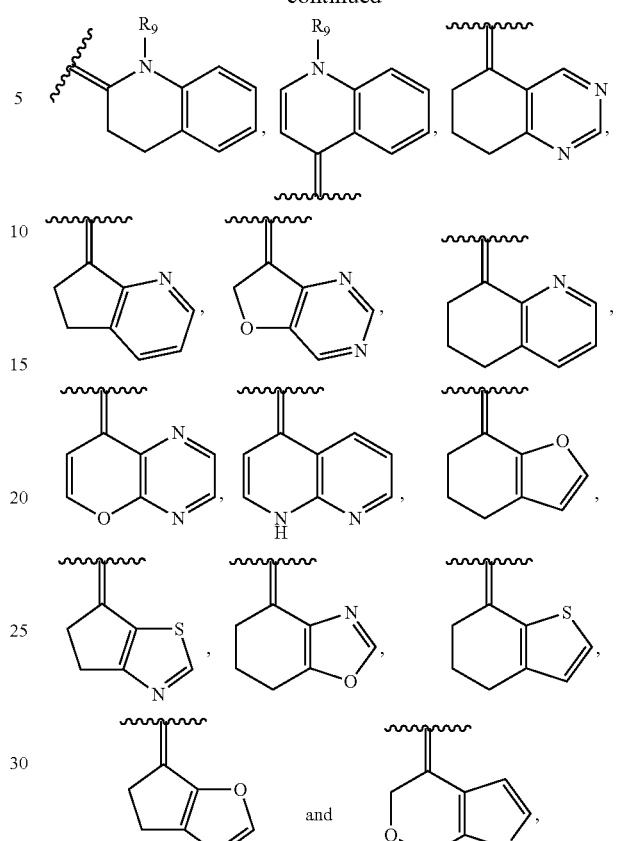
wherein:
each ring system is optionally substituted with one or more substituents;
" ⌇ "
represents the point of attachment; and
$R_9$ is H, an alkyl, an aralkyl, or an alkylcarbonyl.
In some embodiments, the invention relates to compounds of formula (I), (II), (III), or (IV), wherein ring A is a ring system selected from the group consisting of:
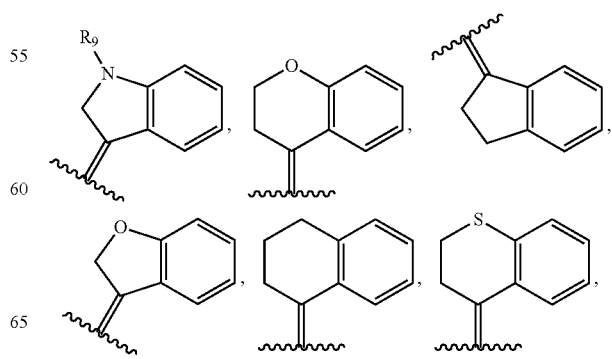

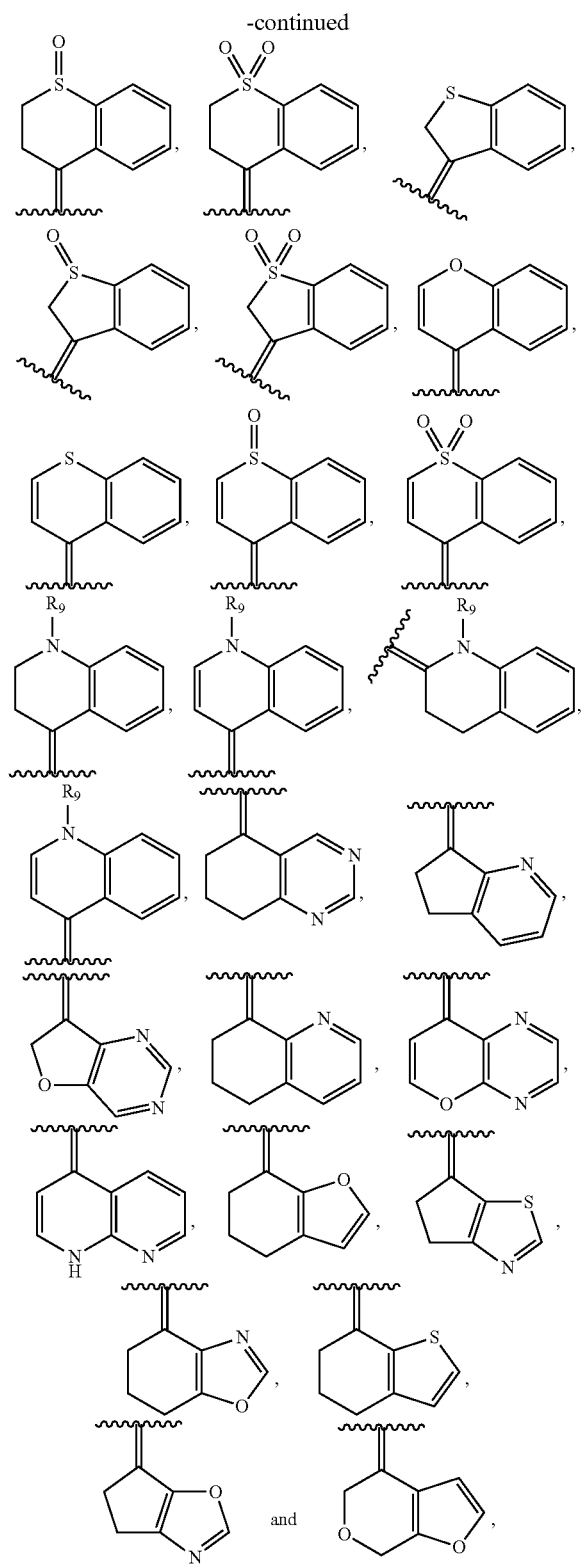

wherein:
each ring system is optionally substituted with one or more substituents.

In some embodiments, the invention relates to compounds of formula (I), (II), (III), or (IV), wherein ring A is optionally substituted with one or more substituents selected from the group consisting of an optionally substituted alkyl, an optionally substituted alkoxy, an optionally substituted alkyl sulfanyl, an optionally substituted alkenyl, an optionally substituted alkynyl, an optionally substituted cycloalkyl, an optionally substituted cyclyl, an optionally substituted heterocyclyl, an optionally substituted heterocycloalkyl, an optionally substituted aryl, an optionally substituted heteroaryl, an optionally substituted aralkyl, an optionally substituted heteraralkyl, a haloalkyl, halo, cyano, nitro, haloalkoxy, =O, =S, =NR, —$OR^k$, —$NR^hR^j$, —$SR^k$, —$C(O)R^k$, —$C(O)NR^hR^j$, —$NR^kC(O)R^k$, —$C(O)OR^k$, —$OC(O)R^k$, —$NR^kC(O)NR^hR^j$, —$OC(O)NR^hR^j$, —$NR^kC(O)OR^k$, —$C(NR)R^k$, —$C(NR)NR^hR^j$, —$NR^kC(NR)R^k$, —$C(NR)OR^k$, —$OC(NR)R^k$, —$NR^kC(NR)NR^hR^j$, —$OC(NR)NR^hR^j$, —$NR^kC(NR)OR^k$, —$C(S)R^k$, —$C(S)NR^hR^j$, —$NR^kC(S)R^k$, —$C(S)OR^k$, —$OC(S)R^k$, —$NR^kC(S)NR^hR^j$, —$OC(S)NR^hR^j$, —$NR^kC(S)OR^k$, —$C(O)SR^k$, —$SC(O)R^k$, —$S(O)_pR^k$, —$S(O)_pNR^hR^j$, —$OS(O)_pR^k$, —$S(O)_pOR^k$, —$OS(O)_pOR^k$, —$P(O)(OR^k)_2$, —$OP(O)(OR^k)_2$, —$P(S)(OR^k)_2$, —$SP(O)(OR^k)_2$, —$P(O)(SR^k)(OR^k)$, —$OP(O)(SR^k)(OR^k)$, —$P(O)(SR^k)_2$, or —$OP(O)(SR^k)_2$, wherein p is 1 or 2.

In some embodiments, the invention relates to compounds of formula (I), (II), (III), or (IV), wherein ring A is optionally substituted with from one to three substituents selected from the group consisting of a lower alkyl, a lower alkoxy, =O, nitro, cyano, hydroxy, amino, lower alkyl amino, lower dialkyl amino, mercapto, lower alkyl sulfanyl, halo, or haloalkyl.

In some embodiments, the invention relates to compounds of formula (I), wherein Y is O.

In some embodiments, the invention relates to compounds of formula (II), (III), or (IV), wherein $Y_1$ is O.

In some embodiments, the invention relates to compounds of formula (I), wherein Y is a covalent bond.

In some embodiments, the invention relates to compounds of formula (II), (III), or (IV), wherein $Y_1$ is a covalent bond.

In some embodiments, the invention relates to compounds of formula (I), wherein $R_3$ is H.

In some embodiments, the invention relates to compounds of formula (I), wherein $R_3$ is an optionally substituted aryl or an optionally substituted heteroaryl.

In some embodiments, the invention relates to compounds of formula (I), wherein $R_3$ is an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl.

In some embodiments, the invention relates to compounds of formula (I), wherein $R_3$ is a hydroxy, an optionally substituted heterocycloalkyl or an optionally substituted heterocyclyl.

In some embodiments, the invention relates to compounds of formula (I), wherein $R_3$ is a hydroxy, an optionally substituted morpholino, or an optionally substituted oxazolidin-2-one.

In some embodiments, the invention relates to compounds of formula (I), wherein each of $R_2$ and $R_4$ is, independently, H, an optionally substituted alkyl, an optionally substituted alkylcarbonyl, an optionally substituted aryl, an optionally substituted heteroaryl, an optionally substituted cycloalkyl, an optionally substituted cyclyl, an optionally substituted heterocycloalkyl, or an optionally substituted heterocyclyl.

In some embodiments, the invention relates to compounds of formula (I), wherein n is 1, 2, or 3, and $R_2$ and $R_4$, for each occurrence are, independently, H or a lower alkyl.

In some embodiments, the invention relates to compounds of formula (I), wherein G is absent.

In some embodiments, the invention relates to compounds of formula (I), wherein G is an optionally substituted heteroaryl or an optionally substituted heterocyclyl.

In some embodiments, the invention relates to compounds of formula (I), wherein G is —C(O)NHNH—, —NHNHC(O)—, —CH=N—NH—, —NH—N=CH—, —NHNH—, —NHO—, —O—NH—, —NR$^k$—O—, —CH=N—O—, —O—N=CH—, —O—C(S)—NH—, or —NH—C(S)—O—.

In some embodiments, the invention relates to compounds of formula (I), wherein G is —O—C(O)—NH—, —NH—C(NH)—NH—, —NR$^k$—C(NH)—NH—, —NR$^k$—C(NR$^k$)—NH—, —NH—C(N(CN))—NH—, —NH—C(NSO$_2$R$^c$)—NH—, —NR$^k$—C(NSO$_2$R$^c$)—NH—, —NH—C(NNO$_2$)—NH—, NH—C(NC(O)R$^c$)—NH—, —NH—C(O)—NH—, or —NH—C(S)—NH—.

In some embodiments, the invention relates to compounds of formula (I), wherein G is —NH—S(O)$_2$—NH—, —NR$^k$—S(O)$_2$O—, —P(O)(R$^c$)—, —P(O)(R$^c$)—O—, or —P(O)(R$^c$)—NR$^k$—.

In some embodiments, the invention relates to compounds of formula (I), wherein G is an optionally substituted cyclyl, an optionally substituted cycloalkyl, an optionally substituted heterocycloalkyl or an optionally substituted heterocyclyl.

In some embodiments, the invention relates to compounds of formula (I), wherein G is an optionally substituted cyclopropyl, an optionally substituted cyclobutyl, an optionally substituted cyclopentyl, an optionally substituted cyclohexyl, an optionally substituted cycloheptyl, an optionally substituted aziridinyl, an optionally substituted oxiranyl, an optionally substituted azetidinyl, an optionally substituted oxetanyl, an optionally substituted morpholinyl, an optionally substituted piperazinyl or an optionally substituted piperidinyl.

In some embodiments, the invention relates to compounds of formula (I), wherein G is an optionally substituted aryl, an optionally substituted heteroaryl, an optionally substituted heteroaralkyl, —C(N—CN)—NH—, —Si(OH)$_2$—, —C(NH)—NR$^k$—, or —NR$^k$—CH$_2$—C(O)—.

In some embodiments, the invention relates to compounds of formula (I), wherein G is an optionally substituted imidazolyl, an optionally substituted imidazolidinone, an optionally substituted imidazolidineamine, an optionally substituted pyrrolidinyl, an optionally substituted pyrrolyl, an optionally substituted furanyl, an optionally substituted thienyl, an optionally substituted thiazolyl, an optionally substituted triazolyl, an optionally substituted oxadiazolyl, an optionally substituted thiadiazolyl, an optionally substituted pyrazolyl, an optionally substituted tetrazolyl, an optionally substituted oxazolyl, an optionally substituted isoxazolyl, an optionally substituted phenyl, an optionally substituted pyridyl, an optionally substituted pyrimidyl, an optionally substituted indolyl, or an optionally substituted benzothiazolyl.

In some embodiments, the invention relates to compounds of formula (I), wherein:
Y is O or CH$_2$;
G is absent; and
n is 0, 1, 2, 3 or 4.

In some embodiments, the invention relates to compounds of formula (I), wherein:
Y is absent, O, S, NR$^k$, or CH$_2$; and
n is 0, 1, 2, 3, or 4.

In some embodiments, the invention relates to compounds of formula (II), wherein:
$X_1$, $X_2$, $Y_1$ is O; and
$R_7$ and $R_8$ are each, independently, H or a lower alkyl.

In some embodiments, the invention relates to compounds of formula (III), wherein:
$X_2$, $X_3$, and $Y_1$ is O;
$R_7$ and $R_8$ are each, independently, H or a lower alkyl.

In some embodiments, the invention relates to compounds of formula (IV), wherein:
$X_2$ and $Y_1$ are O;
$X_4$ is —OH; and
$R_7$ and $R_8$ are each, independently, H or a lower alkyl.

Specific examples of compounds of the invention are set forth below in Table 1:

TABLE 1

| No. | Structure | Name |
|---|---|---|
| 1 | 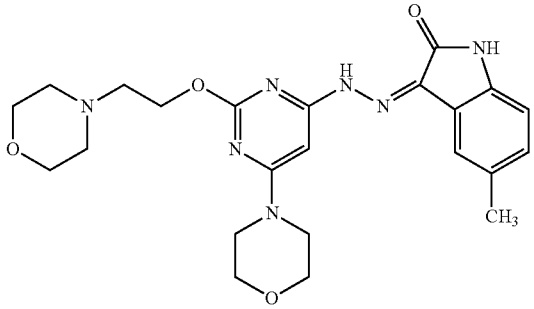 | 5-Methyl-3-{[6-morpholin-4-yl-2-(2-morpholin-4-yl-ethoxy)-pyrimidin-4-yl]-hydrazono}-1,3-dihydro-indol-2-one |

TABLE 1-continued

| No. | Structure | Name |
|---|---|---|
| 2 | 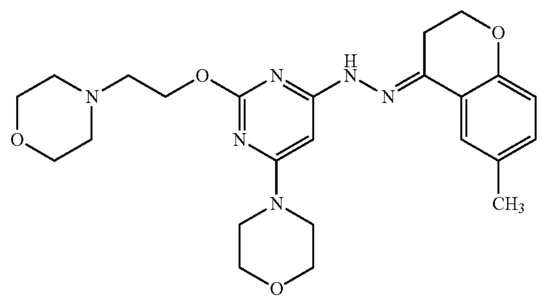 | N-(6-Methyl-chroman-4-ylidene)-N'-[6-morpholin-4-yl-2-(2-morpholin-4-yl-ethoxy)-pyrimidin-4-yl]-hydrazine |
| 3 | 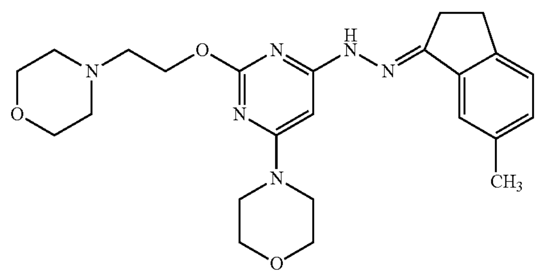 | N-(6-Methyl-indan-1-ylidene)-N'-[6-morpholin-4-yl-2-(2-morpholin-4-yl-ethoxy)-pyrimidin-4-yl]-hydrazine |
| 4 | 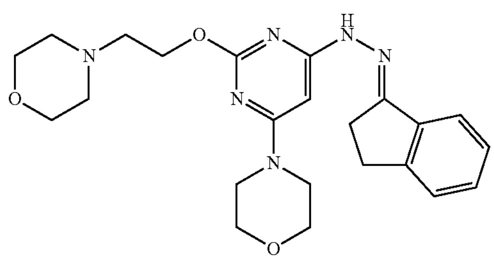 | N-(Indan-1-ylidene)-N'-[6-morpholin-4-yl-2-(2-morpholin-4-yl-ethoxy)-pyrimidin-4-yl]-hydrazine |
| 5 | 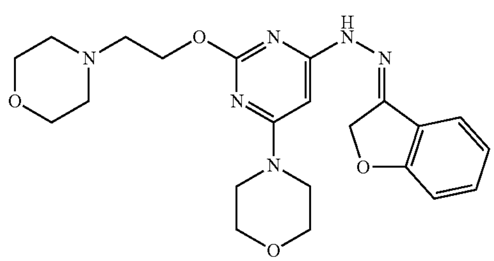 | N-(Benzofuran-3-ylidene)-N'-[6-morpholin-4-yl-2-(2-morpholin-4-yl-ethoxy)-pyrimidin-4-yl]-hydrazine |
| 6 | 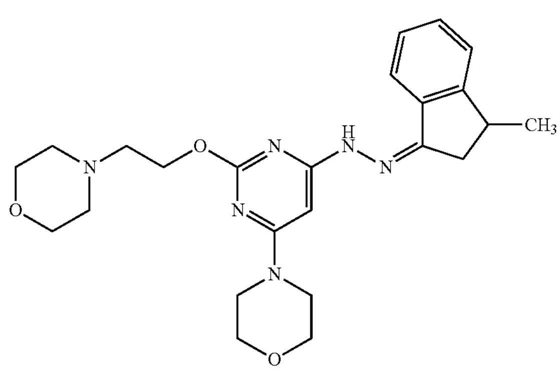 | N-(3-Methyl-indan-1-ylidene)-N'-[6-morpholin-4-yl-2-(2-morpholin-4-yl-ethoxy)-pyrimidin-4-yl]-hydrazine |

TABLE 1-continued

| No. | Structure | Name |
|---|---|---|
| 7 | 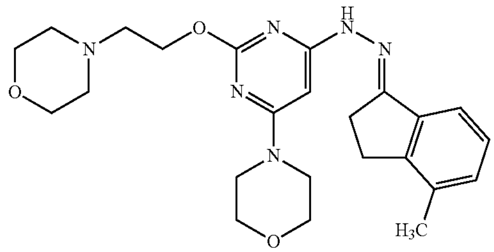 | N-(4-Methyl-indan-1-ylidene)-N'-[6-morpholin-4-yl-2-(2-morpholin-4-yl-ethoxy)-pyrimidin-4-yl]-hydrazine |
| 8 | 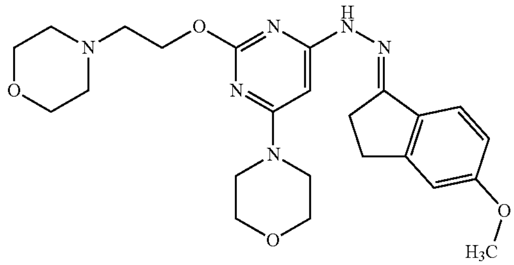 | N-(5-Methoxy-indan-1-ylidene)-N'-[6-morpholin-4-yl-2-(2-morpholin-4-yl-ethoxy)-pyrimidin-4-yl]-hydrazine |
| 9 | 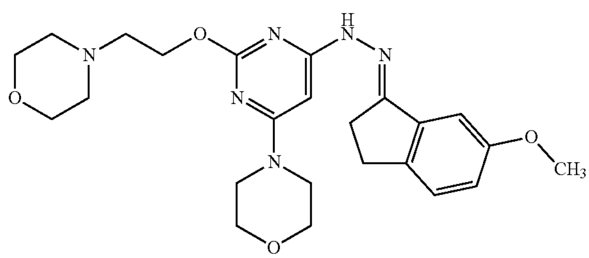 | N-(6-Methoxy-indan-1-ylidene)-N'-[6-morpholin-4-yl-2-(2-morpholin-4-yl-ethoxy)-pyrimidin-4-yl]-hydrazine |
| 10 | 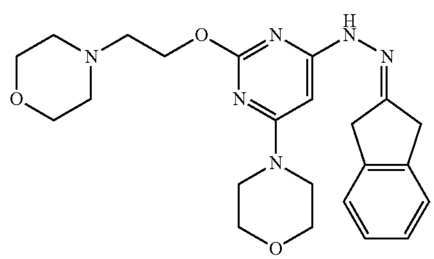 | N-(Indan-2-ylidene)-N'-[6-morpholin-4-yl-2-(2-morpholin-4-yl-ethoxy)-pyrimidin-4-yl]-hydrazine |
| 11 | 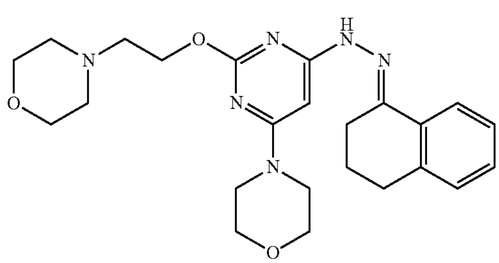 | N-(3,4-Dihydro-2H-naphthalen-1-ylidene)-N'-[6-morpholin-4-yl-2-(2-morpholin-4-yl-ethoxy)-pyrimidin-4-yl]-hydrazine |
| 12 | 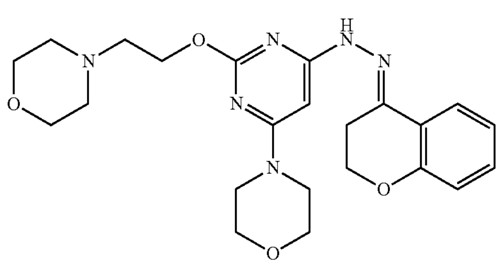 | N-(Chroman-4-ylidene)-N'-[6-morpholin-4-yl-2-(2-morpholin-4-yl-ethoxy)-pyrimidin-4-yl]-hydrazine |

TABLE 1-continued

| No. | Structure | Name |
|---|---|---|
| 13 | 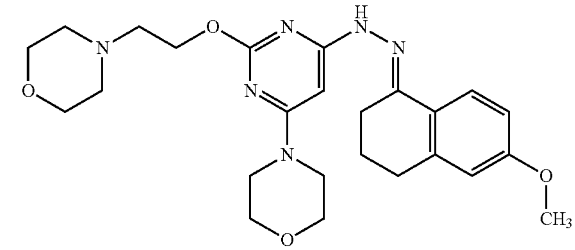 | N-(6-Methoxy-3,4-dihydro-2H-naphthalen-1-ylidene)-N'-[6-morpholin-4-yl-2-(2-morpholin-4-yl-ethoxy)-pyrimidin-4-yl]-hydrazine |
| 14 | 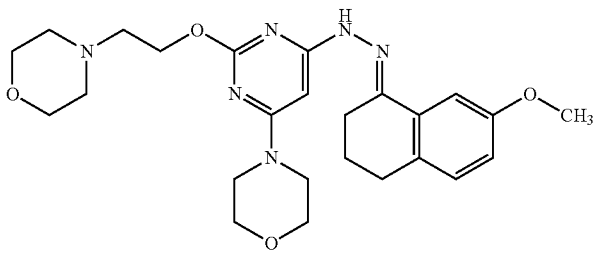 | N-(7-Methoxy-3,4-dihydro-2H-naphthalen-1-ylidene)-N'-[6-morpholin-4-yl-2-(2-morpholin-4-yl-ethoxy)-pyrimidin-4-yl]-hydrazine |
| 15 | 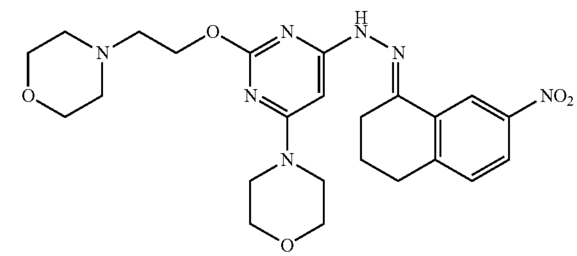 | N-(7-Nitro-3,4-dihydro-2H-naphthalen-1-ylidene)-N'-[6-morpholin-4-yl-2-(2-morpholin-4-yl-ethoxy)-pyrimidin-4-yl]-hydrazine |
| 16 | 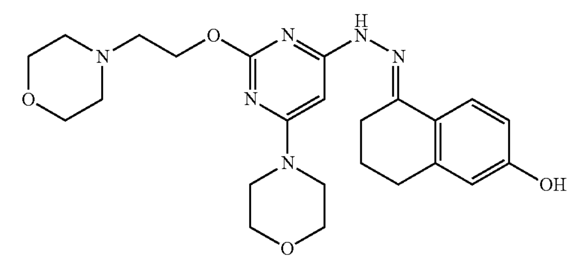 | N-(6-Hydroxy-3,4-dihydro-2H-naphthalen-1-ylidene)-N'-[6-morpholin-4-yl-2-(2-morpholin-4-yl-ethoxy)-pyrimidin-4-yl]-hydrazine |
| 17 | 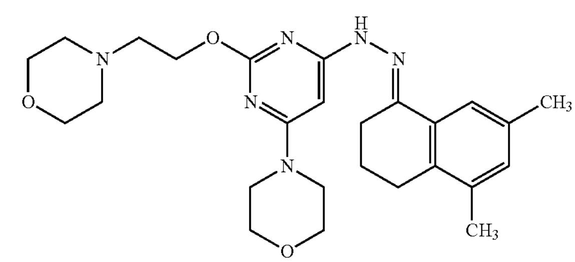 | N-(5,7-Dimethyl-3,4-dihydro-2H-naphthalen-1-ylidene)-N'-[6-morpholin-4-yl-2-(2-morpholin-4-yl-ethoxy)-pyrimidin-4-yl]-hydrazine |
| 18 | 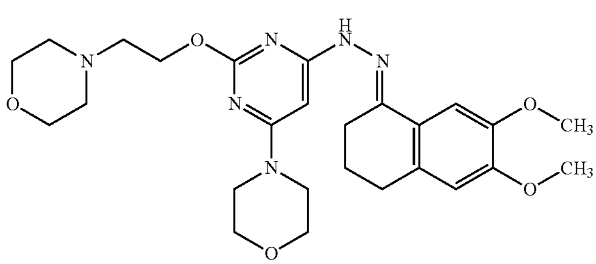 | N-(6,7-Dimethoxy-3,4-dihydro-2H-naphthalen-1-ylidene)-N'-[6-morpholin-4-yl-2-(2-morpholin-4-yl-ethoxy)-pyrimidin-4-yl]-hydrazine |

TABLE 1-continued

| No. | Structure | Name |
|---|---|---|
| 19 | 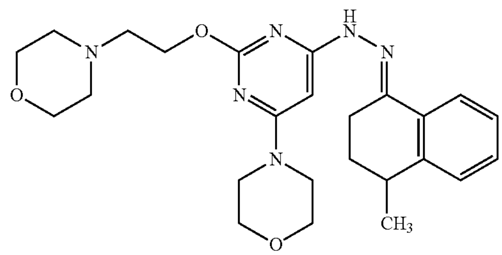 | N-(4-Methyl-3,4-dihydro-2H-naphthalen-1-ylidene)-N'-[6-morpholin-4-yl-2-(2-morpholin-4-yl-ethoxy)-pyrimidin-4-yl]-hydrazine |
| 20 | 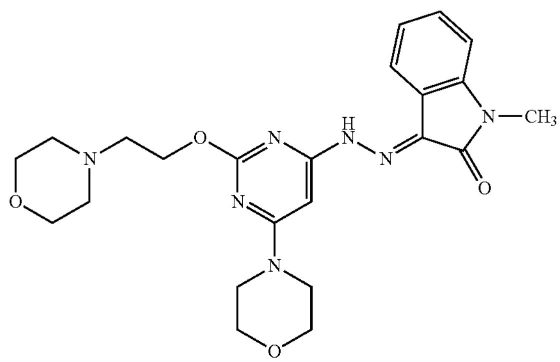 | 1-Methyl-3-{6-[morpholin-4-yl-2-(2-morpholin-4-yl-ethoxy)-pyrimidin-4-yl]-hydrazono}-1,3-dihydro-indol-2-one |
| 21 | 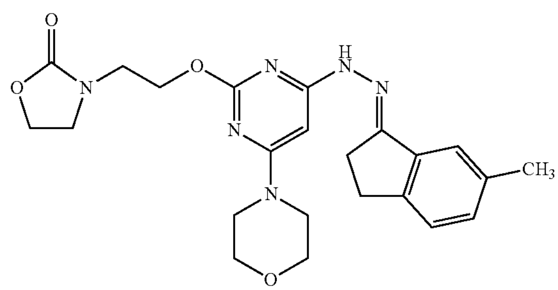 | 3-(2-{4-[N'-(6-Methyl-indan-1-ylidene)-hydrazino]-6-morpholin-4-yl-pyrimidin-2-yloxy}-ethyl)-oxazolidin-2-one |
| 22 | 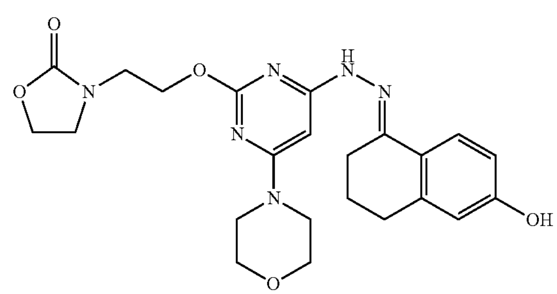 | 3-(2-{4-[N'-(6-Hydroxy-3,4-dihydro-2H-naphthalen-1-ylidene)-hydrazino]-6-morpholin-4-yl-pyrimidin-2-yloxy}-ethyl)-oxazolidin-2-one |
| 23 | 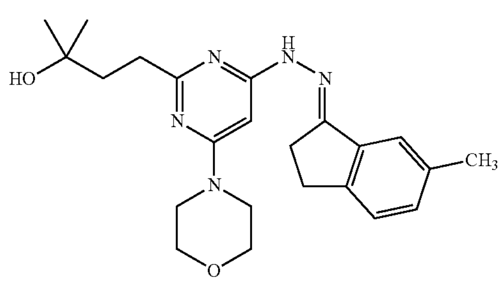 | 2-Methyl-4-{4-[N'-(6-methyl-indan-1-ylidene)-hydrazino]-6-morpholin-4-yl-pyrimidin-2-yloxy}-butan-2-ol |

TABLE 1-continued

| No. | Structure | Name |
|---|---|---|
| 24 | 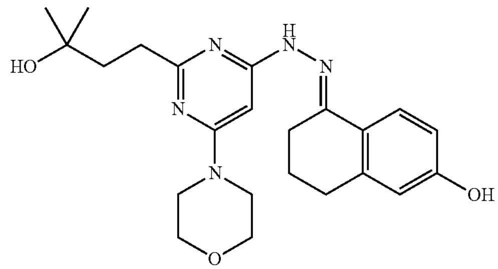 | 5-{[2-(3-Hydroxy-3-methyl-butyl)-6-morpholin-4-yl-pyrimidin-4-yl]-hydrazono}-5,6,7,8-tetrahydro-naphthalen-2-ol |
| 25 | 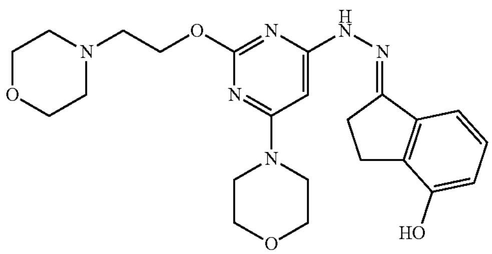 | N-(4-Hydroxy-indan-1-ylidene)-N'-[6-morpholin-4-yl-2-(2-morpholin-4-yl-ethoxy)-pyrimidin-4-yl]-hydrazine |
| 26 | 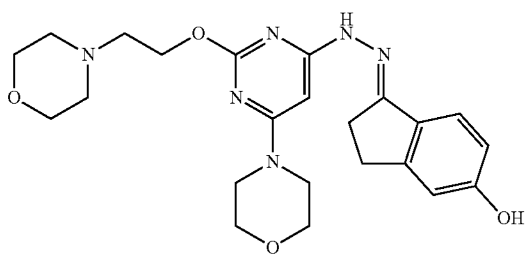 | N-(5-Hydroxy-indan-1-ylidene)-N'-[6-morpholin-4-yl-2-(2-morpholin-4-yl-ethoxy)-pyrimidin-4-yl]-hydrazine |
| 27 | 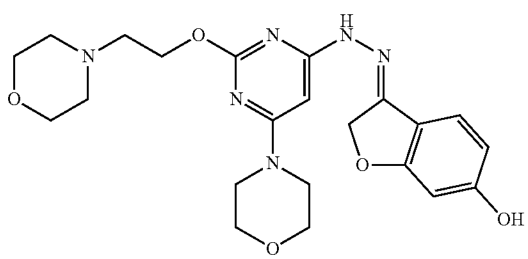 | 3-{[6-Morpholin-4-yl-2-(2-morpholin-4-yl-ethoxy)-pyrimidin-4-yl]-hydrazono}-2,3-dihydro-benzofuran-6-ol |
| 28 | 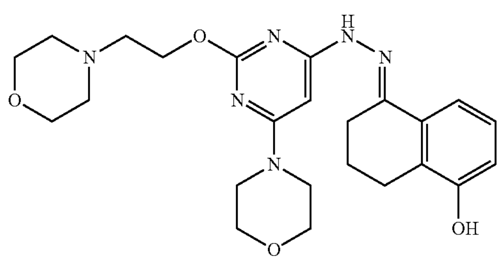 | N-(5-Hydroxy-3,4-dihydro-naphthalen-1-ylidene)-N'-[6-morpholin-4-yl-2-(2-morpholin-4-yl-ethoxy)-pyrimidin-4-yl]-hydrazine |
| 29 | 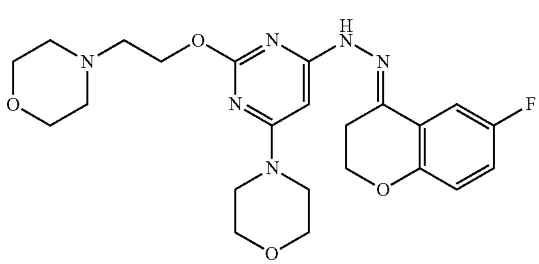 | N-(6-Fluoro-chroman-4-ylidene)-N'-[6-morpholin-4-yl-2-(2-morpholin-4-yl-ethoxy)-pyrimidin-4-yl]-hydrazine |

TABLE 1-continued

| No. | Structure | Name |
|---|---|---|
| 30 | 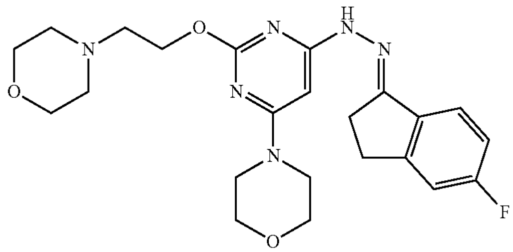 | N-(5-Fluoro-indan-1-ylidene)-N'-[6-morpholin-4-yl-2-(2-morpholin-4-yl-ethoxy)-pyrimidin-4-yl]-hydrazine |
| 31 | 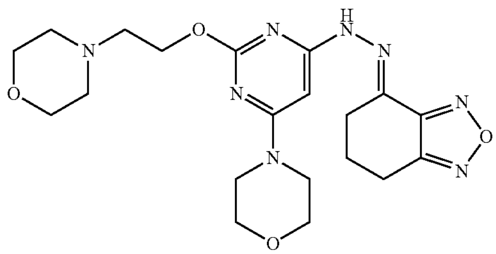 | N-(6,7-Dihydro-5H-benzo[1,2,5]oxadiazol-4-ylidene)-N'-[6-morpholin-4-yl-2-(2-morpholin-4-yl-ethoxy)-pyrimidin-4-yl]-hydrazine |
| 32 | 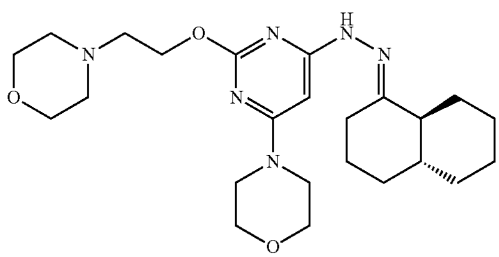 | N-[6-Morpholin-4-yl-2-(2-morpholin-4-yl-ethoxy)-pyrimidin-4-yl]-N'-(octahydro-naphthalen-1-ylidene)-hydrazine |
| 33 | 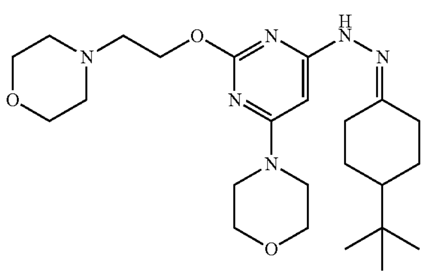 | N-(4-tert-Butyl-cyclohexylidene)-N'-[6-morpholin-4-yl-2-(2-morpholin-4-yl-ethoxy)-pyrimidin-4-yl]-hydrazine |
| 34 | 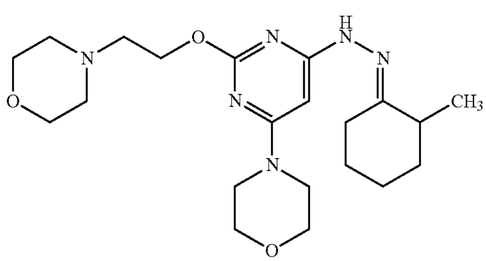 | N-(2-Methyl-cyclohexylidene)-N'-[6-morpholin-4-yl-2-(2-morpholin-4-yl-ethoxy)-pyrimidin-4-yl]-hydrazine |
| 35 | 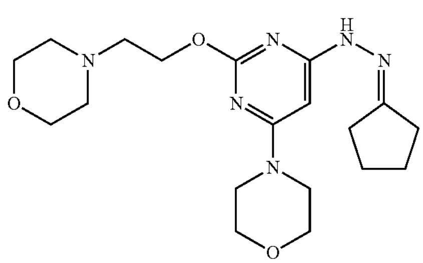 | N-Cyclopentylidene-N'-[6-morpholin-4-yl-2-(2-morpholin-4-yl-ethoxy)-pyrimidin-4-yl]-hydrazine |

TABLE 1-continued

| No. | Structure | Name |
|---|---|---|
| 36 | 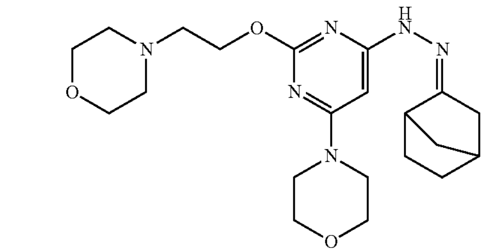 | N-Bicyclo[2.2.1]hept-2-ylidene-N'-[6-morpholin-4-yl-2-(2-morpholin-4-yl-ethoxy)-pyrimidin-4-yl]-hydrazine |
| 37 | 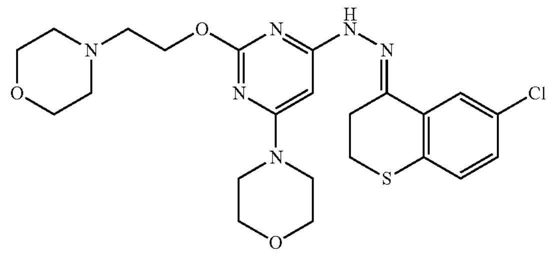 | N-(6-Chloro-thiochroman-4-ylidene)-N'-[6-morpholin-4-yl-2-(2-morpholin-4-yl-ethoxy)-pyrimidin-4-yl]-hydrazine |
| 38 | 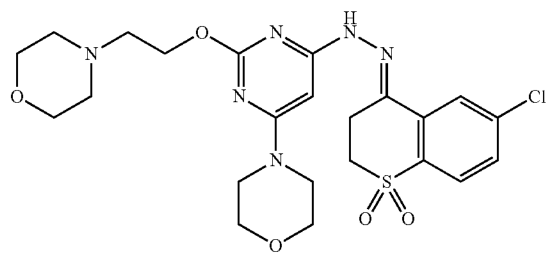 | N-(6-Chloro-1,1-dioxo-1$\lambda^6$-thiochroman-4-ylidene)-N'-[6-morpholin-4-yl-2-(2-morpholin-4-yl-ethoxy)-pyrimidin-4-yl]-hydrazine |
| 39 | 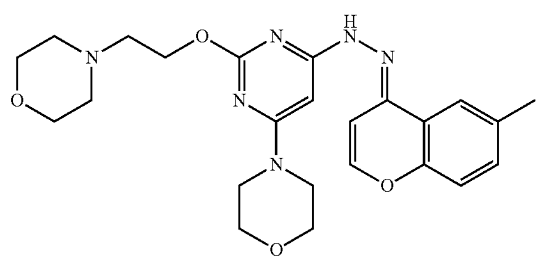 | N-(6-Methyl-chromen-4-ylidene)-N'-[6-morpholin-4-yl-2-(2-morpholin-4-yl-ethoxy)-pyrimidin-4-yl]-hydrazine |
| 40 | 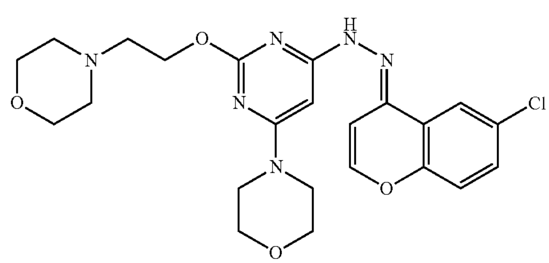 | N-(6-Chloro-chromen-4-ylidene)-N'-[6-morpholin-4-yl-2-(2-morpholin-4-yl-ethoxy)-pyrimidin-4-yl]-hydrazine |
| 41 | 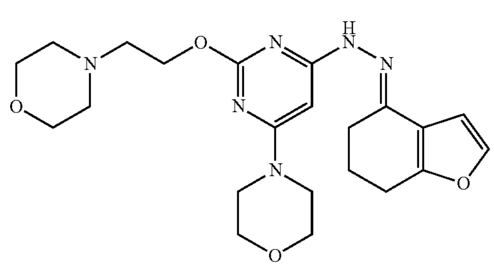 | N-(6,7-Dihydro-5H-benzofuran-4-ylidene)-N'-[6-morpholin-4-yl-2-(morpholin-4-yl-ethoxy)-pyrimidin-4-yl]-hydrazine |

All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features feature, embodiments or substituents.

In another aspect, the invention provides a method of inhibiting IL-12 production in a subject. The method includes the step of administering to the subject an effective amount of a compound of the invention (e.g., a compound of formula (I), (II), (III), (IV) or Table 1, including a pharmaceutically acceptable salt, solvate, clathrate, hydrate, polymorph or prodrug thereof).

In another aspect, the invention provides a method for treating or preventing an interleukin-12 over-production-related disorder. The method includes the step of administering to a subject in need thereof an effective amount of a compound of the invention (e.g., a compound of formula (I), (II), (III), (IV) or Table 1, including a pharmaceutically acceptable salt, solvate, clathrate, hydrate, polymorph or prodrug thereof). In preferred embodiments, the disorder is selected from the group consisting of multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease. In certain embodiments, the disorder is rheumatoid arthritis, sepsis, Crohn's disease, multiple sclerosis, psoriasis, psoriatic arthritis, or immune-mediated diabetes mellitus.

In still another aspect, the invention provides a method for treating or preventing disorders associated with excessive bone loss, the method comprising administering to a subject in need thereof an effective amount of a compound of the invention (e.g., a compound of formula (I), (II), (III), (IV) or Table 1, including a pharmaceutically acceptable salt, solvate, clathrate, hydrate, polymorph or prodrug thereof). In certain embodiments, the disorder is periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteoporosis, hypercalcemia of malignancy (HCM), osteolytic bone lesions of multiple myeloma and osteolytic bone metastases of breast cancer, and metastatic cancers.

In still another aspect, the invention provides a method for inhibiting osteoclast formation in vitro or in vivo, the method comprising contacting a pre-osteoclast cell with an effective amount of a compound of the invention (e.g., a compound of formula (I), (II), (III), (IV) or Table 1, including apharmaceutically acceptable salt, solvate, clathrate, hydrate, polymorph or prodrug thereof).

In yet another aspect, the invention provides a method of treating or preventing a disorder associated with excessive bone resorption by osteoclasts in a subject in need thereof, the method comprising administering to the subject an effective amount of a compound of the invention (e.g., a compound of formula (I), (II), (III), (IV) or Table 1, including a pharmaceutically acceptable salt, solvate, clathrate, hydrate, polymorph or prodrug thereof).

In still another aspect, the invention provides a method of inhibiting proliferation of $T_H1$ cells in a subject comprising administering to the subject an effective amount of a compound of the invention (e.g., a compound of formula (I), (II), (III), (IV) or Table 1, including a pharmaceutically acceptable salt, solvate, clathrate, hydrate, polymorph or prodrug thereof).

In still another aspect, the invention provides a method of inhibiting IL-23 production in a subject, comprising administering to the subject an effective amount of a compound of formula (I), (II), (III), (IV), or Table 1, including a pharmaceutically acceptable salt, solvate, clathrate, hydrate, polymorph or prodrug thereof. In preferred embodiments, the method further includes inhibiting the production of IL-12 and/or inhibiting $T_H1$ lymphocyte proliferation.

In yet another aspect, the invention provides a method of inhibiting IL-27 production in a subject, comprising administering to the subject an effective amount of a compound of formula (I), (II), (III), (IV), or Table 1, including a pharmaceutically acceptable salt, solvate, clathrate, hydrate, polymorph or prodrug thereof. In certain embodiments, the method further includes inhibiting $T_H1$ lymphocyte proliferation, and/or further includes inhibiting the production of IL-12.

In still another aspect, the invention provides a method of treating or preventing an inflammatory disorder in a subject in need of such treatment, the method comprising administering to the subject an effective amount of a compound of the invention (e.g., a compound of formula (I), (II), (III), (IV), or Table 1, including a pharmaceutically acceptable salt, solvate, clathrate, hydrate, polymorph or prodrug thereof).

In still another aspect, the invention provides a method of treating or preventing an immune disease in a subject in need of such treatment, the method comprising administering to the subject an effective amount of a compound of the invention (e.g., a compound of formula (I), (II), (III), (IV), or Table 1, including a pharmaceutically acceptable salt, solvate, clathrate, hydrate, polymorph or prodrug thereof).

In still another aspect, the invention provides a method of treating or preventing a neurological disorder in a subject in need of such treatment, the method comprising administering to the subject an effective amount of a compound of the invention (e.g., a compound of formula (I), (II), (III), (IV), or Table 1, including a pharmaceutically acceptable salt, solvate, clathrate, hydrate, polymorph or prodrug thereof).

Other embodiments include the compounds, intermediates, or a pharmaceutically acceptable salt, solvate, clatharate, hydrate, polymorph or prodrug thereof delineated herein, or compositions including them; as well as their methods of use for treatment or prevention of disease, inhibition of IL-12, or modulation of IL-12 mediated disease; and methods of making the compounds and intermediates herein.

Another embodiment is a method of making a compound of any of the formulae herein using any one, or combination of, reactions delineated herein. The method can include the use of one or more intermediates or chemical reagents delineated herein.

Another aspect is a radiolabeled compound of any of the formulae delineated herein. Such compounds have one or more radioactive atoms (e.g., $^3H$, $^2H$, $^{14}C$, $^{13}C$, $^{32}P$, $^{35}S$, $^{125}I$, and $^{131}I$) introduced into the compound. Such compounds are useful for drug metabolism studies and diagnostics.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy," as used herein, refers to an alkyl or a cycloalkyl group which is linked to another moiety though an oxygen atom. Alkoxy groups can be optionally substituted with one or more substituents.

The term "mercapto" refers to a —SH group.

The term "alkyl sulfanyl," as used herein, refers to an alkyl or a cycloalkyl group which is linked to another moiety though a divalent sulfur atom. Alkyl sulfanyl groups can be optionally substituted with one or more substituents.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system which is completely saturated ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, cyclodecyl, and bicyclo[2.1.1]hexyl.

The term "cyclyl" refers to a hydrocarbon 3-8 membered monocyclic or 7-14 membered bicyclic ring system having at least one non-aromatic ring, wherein the non-aromatic ring has some degree of unsaturation. Cyclyl groups may be optionally substituted with one or more substituents. In one embodiment, 0, 1, 2, 3, or 4 atoms of each ring of a cyclyl group may be substituted by a substituent. Examples of cyclyl groups include cyclohexenyl, bicyclo[2.2.1]hept-2-enyl, dihydronaphthalenyl, benzocyclopentyl, cyclopentenyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a $(C_1-C_6)$alkylene group. Aralkyl groups may be optionally substituted, either on the aryl portion of the aralkyl group or on the alkylene portion of the aralkyl group, with one or more substituent. Representative aralkyl groups include benzyl, 2-phenyl-ethyl, naphth-3-yl-methyl and the like.

As used herein, the term "alkylene" refers to an alkyl group that has two points of attachment. The term "$(C_1-C_6)$alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH$($CH_3$)—), and the like. Alkylene groups may be optionally substituted.

As used herein, the term "cycloalkylene" refers to a cycloalkyl group that has two points of attachment. Cycloalkylene groups may be optionally substituted.

As used herein, the term "cyclylene" refers to a cyclyl group that has two points of attachment. Cyclylene groups may be optionally substituted.

As used herein, the term "arylene" refers to an aryl group that has two points of attachment. Arylene groups may be optionally substituted.

As used herein, the term "aralkylene" refers to an aralkyl group that has two points of attachment. Aralkylene groups may be optionally substituted.

The term "arylalkoxy" refers to an alkoxy substituted with an aryl.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a $(C_1-C_6)$alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

As used herein, the term "heteroarylene" refers to a heteroaryl group that has two points of attachment. Heteroarylene groups may be optionally substituted.

As used herein, the term "heteroaralkylene" refers to a heteroaralkyl group that has two points of attachment. Heteroaralkylene groups may be optionally substituted.

The term "heterocycloalkyl" refers to a nonaromatic, completely saturated 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, an thiirene.

The term "heterocyclyl" refers to a nonaromatic 5-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d]1,2,4-oxadiazolyl, 7H-oxazolo[3,2-d]1,2,4-oxadiazolyl, and the like.

As used herein, the term "heterocycloalkylene" refers to a heterocycloalkyl group that has two points of attachment. Heterocycloalkylene groups may be optionally substituted.

As used herein, the term "heterocyclylene" refers to a heterocyclyl group that has two points of attachment. Heterocyclylene groups may be optionally substituted.

When a cycloalkyl, cyclyl, heterocycloalkyl, or heterocyclyl is fused to another ring (e.g., a cycloalkyl, cyclyl, heterocycloalkyl, heterocyclyl, aryl, heteroaryl), it shares two or more ring atoms, preferably two to four ring atoms, with the other ring.

The term "amino" refers to —NH$_2$. The term "alkylamino" refers to an amino in which one hydrogen is replaced by an alkyl group. The term "dialkylamino" refers to an amino in which each of the hydrogens is replaced by an independently selected alkyl group. The term "aminoalkyl" refers to an alkyl substituent which is further substituted with one or more amino groups.

The term "mercaptoalkyl" refers to an alkyl substituent which is further substituted with one or more mercapto groups.

The term "hydroxyalkyl" or "hydroxylalkyl" refers to an alkyl substituent which is further substituted with one or more hydroxy groups.

The term "sulfonylalkyl" refers to an alkyl substituent which is further substituted with one or more sulfonyl groups.

The term "sulfonylaryl" refers to an aryl substituent which is further substituted with one or more sulfonyl groups.

The term alkylcarbonyl refers to an —C(O)-alkyl.

The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Suitable substituents for an alkyl, alkoxy, alkyl sulfanyl, alkylamino, dialkylamino, alkylene, alkenyl, alkynyl, cycloalkyl, cyclyl, heterocycloalkyl, heterocyclyl, aryl, aralkyl, heteroaryl, heteroaralkyl, cycloalkylene, cyclylene, heterocycloalkylene, heterocyclylene, arylene, aralkylene, heteroalkylene and heteroaryalkylene groups include any substituent which will form a stable compound of the invention. Examples of substituents for an alkyl, alkoxy, alkylsulfanyl, alkylamino, dialkylamino, alkylene, alkenyl, alkynyl, cycloalkyl, cyclyl, heterocycloalkyl, heterocyclyl, aryl, aralkyl, heteroaryl, heteroaralkyl, cycloalkylene, cyclylene, heterocycloalkylene, heterocyclylene, arylene, aralkylene, heteroalkylene and heteroaryalkylene include an optionally substituted alkyl, an optionally substituted alkoxy, an optionally substituted alkyl sulfanyl, an optionally substituted alkenyl, an optionally substituted alkynyl, an optionally substituted cycloalkyl, an optionally substituted cyclyl, an optionally substituted heterocyclyl, an optionally substituted heterocycloalkyl, an optionally substituted aryl, an optionally substituted heteroaryl, an optionally substituted aralkyl, an optionally substituted heteraralkyl, a haloalkyl, halo, cyano, nitro, haloalkoxy, =O, =S, =NR, —OR$^k$, —NR$^h$R$^j$, —SR$^k$, —C(O)R$^k$, —C(O)NR$^h$R$^j$, —NR$^k$C(O)R$^k$, —C(O)OR$^k$, —OC(O)R$^k$, —NR$^k$C(O)NR$^h$R$^j$, —OC(O)NR$^h$R$^j$, —NR$^k$C(O)OR$^k$, —C(NR)R$^k$, —C(NR)NR$^h$R$^j$, —NR$^k$C(NR)R$^k$, —C(NR)OR$^k$, —OC(NR)R$^k$, —NR$^k$C(NR)NR$^h$R$^j$, —OC(NR)NR$^h$R$^j$, —NR$^k$C(NR)OR$^k$, —C(S)R$^k$, —C(S)NR$^h$R$^j$, —NR$^k$C(S)R$^k$, —C(S)OR$^k$, —OC(S)R$^k$, —NR$^k$C(S)NR$^h$R$^j$, —OC(S)NR$^h$R$^j$, —NR$^k$C(S)OR$^k$, —C(O)SR$^k$, —SC(O)R$^k$, —S(O)$_p$R$^k$, —S(O)$_p$NR$^h$R$^j$, —OS(O)$_p$R$^k$, —S(O)$_p$OR$^k$, —OS(O)$_p$OR$^k$, —P(O)(OR$^k$)$_2$, —OP(O)(OR$^k$)$_2$, —P(S)(OR$^k$)$_2$, —SP(O)(OR$^k$)$_2$, —P(O)(SR$^k$)(OR$^k$), —OP(O)(SR$^k$)(OR$^k$), —P(O)(SR$^k$)$_2$, or —OP(O)(SR$^k$)$_2$, wherein p is 1 or 2.

In addition, alkyl, cycloalkyl, alkylene, a heterocycloalkyl, a and any saturated portion of a alkenyl, a cyclyl, alkynyl, heterocyclyl, aralkyl, and heteroaralkyl groups, may also be substituted with =O, =S, or =NR.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6-carbon atoms, respectively. A "lower alkoxy" or "lower alkyl sulfanyl" group refers to an alkoxy or alkyl sulfanyl group that has from 1 to 6 carbon atoms.

In the compounds represented by formula (I), when n is 2 or greater, a compound of the invention may have two or more $C(R_2R_4)$ moieties which can be the same or different. Likewise, in formulas (II), (III) and (IV), when q is 2 or greater, a compound of the invention may have two or more $C(R_7R_8)$ moieties which can be the same or different. When there are more than one group having a designation (e.g., $R^c$-containing substituted groups) in a compound of the invention, the moieties (e.g., $R^c$) can be the same or different. The same rules apply to other R-groups (e.g., R, $R^c$, $R^g$, $R^h$, $R^j$, $R^k$, $R_2$, $R_4$, $R_7$, $R_8$, etc).

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating IL-12 overproduction-related disorders such as rheumatoid arthritis, sepsis, Crohn's disease, multiple sclerosis, psoriasis, psoriatic arthritis, or insulin-dependent diabetes mellitus). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography, etc.). Other embodiments relate to the intermediate compounds delineated herein, and their use in the methods (e.g., treatment, synthesis) delineated herein.

The compounds of this invention include the compounds themselves, as well as their salts, solvate, clathrate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by 1 BURGER's MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Further, the aforementioned compounds also include their N-oxides. The term "N-oxides" refers to one or more nitrogen atoms, when present in a heterocyclic or heteroaryl compound, are in TV-oxide form, i.e., N→O. For example, in compounds of formula (I), (II), (III), (IV), or Table 1 when one of Q, U, or V is N, also included are compounds in which Q, U, or V, respectively, is N→O.

As used herein, the term "pharmaceutically acceptable solvate," is a solvate formed from the association of one or more solvent molecules to one of the compounds of formula (I), (II), (III), (IV) or Table 1. The term solvate includes hydrates (e.g., hemi-hydrate, mono-hydrate, dihydrate, trihydrate, tetrahydrate, and the like).

As used herein, the term "pre-osteoclast cell" is a cell capable of forming an osteoclast cell upon differentiation and/or fusion and includes without limitation, circulating monocytes and tissue macrophages (N. Kurihara et al., Endocrinology 126: 2733-41 (1990)). Without wishing to be bound by theory, pre-osteoclasts are converted to activated osteoclasts in a process thought to involve two factors produced by pre-osteoblasts, M-CSF and ODF. These factors activate certain genes that are needed for the conversion of a pre-osteoclast into an osteoclast.

Also within the scope of this invention is a pharmaceutical composition that contain a pharmaceutically acceptable carrier or diluent and an effective amount of one or more of the compounds of this invention or a pharmaceutically acceptable salt, solvate, clathrate, or prodrug thereof. The compounds described herein are useful to treat and prevent any IL-12 production-related disorders, e.g., inflammatory disorders, immune diseases, neurological disorders and bone loss diseases.

The compounds of the invention are particularly useful in inhibiting the production of IL-12 and/or inhibiting the production of cytokines such as IL-23 and IL-27 which stimulate and/or otherwise augment the production of IL-12 and/or the proliferation of $T_H1$ lymphocytes. Thus, in one aspect, the present invention provides a method of inhibiting the production of IL-12 and/or inhibiting the production of a cytokine that stimulates or facilitates the production of IL-12 (e.g., IL-23 and IL-27) in a subject by administering to the subject an effective amount of a compound of any of the formulae herein, or a pharmaceutically acceptable salt, solvate, clathrate, hydrate, polymorph, or prodrug thereof.

Since the function of LL-12 is induction of INF-γ expression from T and NK cells which promotes the development of $T_H1$ T lymphocyte type, the compounds of the invention can be used to inhibit the production of $T_H1$ cells. Therefore, in one aspect, the invention features a method of inhibiting the production and/or development of $T_H1$ cells in a subject by administering to the subject an effective amount of a compound of any of the formulae herein, or a pharmaceutically acceptable salt, solvate, clathrate, hydrate, polymorph, or prodrug thereof.

In another aspect, the invention provides method for treating an interleukin-12 production-related disorder, comprising administering to a subject in need thereof an effective amount of a compound of any of the formulae herein, or a pharmaceutically acceptable salt, solvate, clathrate, hydrate, polymorph, or prodrug thereof. In certain embodiments, the disorder is selected from the group consisting of multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease, more preferably rheumatoid arthritis, sepsis, Crohn's disease, multiple sclerosis, psoriasis, or immune-mediated diabetes mellitus.

The term "inflammatory disorders" includes any inflammatory disease, disorder or condition caused, exasperated or mediated by IL-12 production. Such inflammatory disorders may include, without limitation, asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

1. "Inflammatory disorders" expressly include acute inflammatory disorders. Examples of acute inflammatory disorders include graft versus host disease, transplant rejection, septic shock, endotoxemia, Lyme arthritis, infectious meningitis (e.g., viral, bacterial, Lyme disease-associated), an acute episode of asthma and acute episodes of an autoimmune disease.

2. "Inflammatory disorders" expressly include chronic inflammatory disorders. Nonlimiting examples of chronic inflammatory disorder include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

3. The term "immune disease" or "immune disorder" includes any immune disease, disorder or condition caused, exasperated or mediated by IL-12 production. Such immune diseases may include, without limitation, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersentitity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

4. In one aspect, the invention provides method for treating a neurological disorder, comprising administering to a subject in need thereof an effective amount of a compound of any of the formulae herein, or a pharmaceutically acceptable salt, solvate, clathrate, hydrate, polymorph, or prodrug thereof. The term "neurological disorder" includes any neurological disease, disorder or condition caused, exasperated or mediated by IL-12 production. Such neurological disorders may include, without limitation, neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Optionally, such a method can also comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16, Edition, Merck & Company, Rahway, N.J. (1992)

5. In the case of overlap in these definitions, the disease, condition or disorder may be considered to be a member of any of the above listed classes of IL-12 production-related disorders.

Although the mechanism is not yet understood, compounds of the invention have been found to inhibit the formation of osteoclasts (see co-owned PCT Application Number US04/17064 filed on May 28, 2004, the entire teachings of which are incorporated herein by reference). Osteoclasts are unique multinucleated cells within bone that are responsible for bone degradation and resorption. These are the only cells in the body known to be capable of this function. The regulation of osteoclastic formation and activity is only partly understood but it is known that excessive bone resorption by osteoclasts contributes to the pathology of many human diseases associated with excessive bone loss. Thus, in one aspect, the invention provides a method of treating or preventing disorders associated with excessive bone loss, comprising administering to a subject in need thereof a therapeutically effective amount of a compound of any of the formulae herein or pharmaceutically acceptable salt, solvate, clathrate, hydrate, polymorph, or prodrug thereof. Disorders associated with excessive bone loss include, but are not limited to periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteoporosis, hypercalcemia of malignancy (HCM), osteolytic bone lesions of multiple myeloma and osteolytic bone metastases of breast cancer, and metastatic cancers. The method includes administering to a subject (e.g., a human or an animal) in need thereof an effective amount of one or more compounds of formula (I), (II), (III), (IV), or Table 1, or a pharmaceutically acceptable salt, solvate, clathrate, or prodrug thereof, or a pharmaceutical composition having an effective amount of one or more compounds of formula (I), (II), (III), (IV), or Table 1, or a pharmaceutically acceptable salt, solvate, clathrate, or prodrug thereof.

In another aspect, this invention features methods for inhibiting osteoclast formation in vitro or in vivo. The method includes contacting a pre-osteoclast cell (e.g., a cell capable of forming an osteoclast cell upon differentiation and/or fusion) with an effective amount of a compound of formula (I), (II), (III), (IV), or Table 1, or a pharmaceutically acceptable salt, solvate, clathrate, or prodrug thereof or a pharmaceutical composition comprising an effective amount of a compound of formula (I), (II), (III), (IV), or Table 1, or a pharmaceutically acceptable salt, solvate, clathrate, or prodrug thereof.

In a further aspect, this invention features methods of treating or preventing a disorder associated with excessive bone resorption by osteoclasts in a subject in need thereof. The method includes administering to a subject (e.g., a human or an animal) in need thereof an effective amount of one or more compounds of formula (I), (II), (III), (IV), or Table 1, or a pharmaceutically acceptable salt, solvate, clathrate, or prodrug thereof, or a pharmaceutical composition having an effective amount of one or more compounds of formula (I), (II), (III), (IV), or Table 1, or a pharmaceutically acceptable salt, solvate, clathrate, or prodrug thereof.

In another aspect, the invention provides a method for inhibiting osteoclast formation in vitro or in vivo, comprising contacting a pre-osteoclast cell with an effective amount of a compound of any of the formulae herein or pharmaceutically acceptable salt, solvate, clathrate, hydrate, polymorph, or prodrug thereof.

The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

Other embodiments include the compounds, intermediates, or a pharmaceutically acceptable salt, solvate, clatharate, hydrate, polymorph, or prodrug thereof delineated herein, or compositions including them; as well as their methods of use for treatment or prevention of disease, inhibition of IL-12, or modulation of IL-12 mediated disease.

Another embodiment is a method of making a compound of any of the formulae herein using any one, or combination of, reactions delineated herein. The method can include the use of one or more intermediates or chemical reagents delineated herein.

As used herein, the terms "treat", "treatment" and "treating" refer to the reduction or amelioration of the progression, severity and/or duration of an inflammatory disorder, immune diseases, bone loss disease, or a neurological disorder, or the amelioration of one or more symptoms (preferably, one or more discernible symptoms) of an inflammatory disorder, immune diseases, bone loss disease, or a neurological disorder resulting from the administration of one or more therapies (e.g., one or more therapeutic agents such as a compound of the invention).

As used herein, the terms "prevent", "prevention" and "preventing" refer to the reduction in the risk of acquiring or developing a given inflammatory disorder, immune diseases, bone loss disease, or a neurological disorder, or the reduction or inhibition of the recurrence, onset or development of one or more symptoms of a given inflammatory disorder, immune diseases, bone loss disease, or a neurological disorder. In a preferred embodiment, a compound of the invention is administered as a preventative measure to a patient, preferably a human, having a genetic predisposition to any of the disorders described herein.

As used herein, the term "effective amount" refers to an amount of a compound of this invention which is sufficient to reduce or ameliorate the severity, duration, progression, or onset of an inflammatory disorder, immune diseases, bone loss disease, or neurological disorder, prevent the advancement of an inflammatory disorder, immune diseases, bone loss disease, or neurological disorder, cause the regression of an inflammatory disorder, immune diseases, bone loss disease, or neurological disorder, prevent the recurrence, development, onset or progression of a symptom associated with an inflammatory disorder, immune diseases, bone loss disease, or neurological disorder, or enhance or improve the prophylactic or therapeutic effect(s) of another therapy. In certain preferred embodiments, treatment according to the invention provides a reduction in, or prevention of, at least one symptom or manifestation of an IL-12-, IL-23-, or IL-27-related disorder (e.g., inflammatory disorder, immune diseases, bone loss disease, or neurological disorder), as determined in vivo or in vitro of at least about 10%, more preferably 20%, 30%, 40%, 50%, 60%, 70%, 80%, 90%, 95%, 98% or 99%. In certain preferred embodiments, treatment according to the invention provides a reduction in IL-12-, IL-23-, or IL-27 production, as determined in vivo or in vitro by at least about 5%, more preferably 10%, 20%, 30%, 40%, 50%, or more when compared to the patient's levels of IL-12-, IL-23-, or IL-27 before treatment with a compound of the invention.

The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the pyridine compound of this invention can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

To practice a method of the present invention, a compound of the invention, alone, or as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A heterocyclic compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the compounds of the invention. Examples of other carriers include colloidal silicon dioxide, magnesium stearate, cellulose, sodium lauryl sulfate, and D&C Yellow #10.

As used herein, the terms "animal", "subject," "mammal" and "patient", include, but are not limited to, a cow, monkey, horse, sheep, pig, chicken, turkey, quail, cat, dog, mouse, rat, rabbit, guinea pig and human (preferably, a human).

The methods for treating or preventing disorders associated with excessive bone loss in a patient in need thereof can further comprise administering to the patient being administered a compound of this invention, an effective amount of one or more other therapeutic agents. Such therapeutic agents may include other therapeutic agents such as those conventionally used to prevent or treat disorders associated with excessive bone resorption or symptoms thereof. For example, such other agents include anti-resorptive agents for example progestins, polyphosphonates, bisphosphonate(s), estrogen agonists/antagonists, estrogen (such as Premarin®), estrogen/progestin combinations, and estrogen derivatives (such as estrone, estriol or 17α, 17β-ethynyl estradiol).

In such combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective amount would be where the other therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, dthynodiol diacetate, etonogestrel, fluorogestone acetate, gestaclone, gestodene, gestonorone caproate, gestrinone, haloprogesterone, hydroxyprogesterone, caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type disclosed in U.S. Pat. No. 3,683,080. Preferred polyphosphonates are geminal dipolyphosphonates (also referred to as bis-phosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-biphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used for this purpose. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue; and blocking the actions of estrogen in one or more tissues. Such activities are readily determined by those skilled in the art of standard assays including estrogen receptor binding assays, standard bone histomorphometric and densitometer methods, and E. F Eriksen et al., Bone Histomorphometry, Raven Press, New York, pp. 1-74 (1994); S. J. Grier et. al., The Use of Dual-Energy X-Ray Absorptiometry In Animals, Inv. Radiol. 31(1): 50-62 (1996); Wahner H. W. and Fogelman I., The Evaluation of Osteoporosis: Dual Energy X-Ray Absorptiometry in Clinical Practice., Martin Dunitz Ltd., London, pp. 1-296 (1994)). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431. Another preferred estrogen agonist/antagonist is 3-(4-(1,2-diphenyl-but-1-enyl)-phenyl)-acrylic acid, which is disclosed in Wilson et al., Endocrinology 138: 3901-11 (1997). Another preferred estrogen agonist/antagonist is tamoxifen: (ethanamine,2-(-4-(1,2-diphenyl-1-butenyl)phenoxy)-N,N-dimethyl, (Z)-2-,2-hydroxy-1,2,3-propanetricarboxylate(1:1)) and related compounds which are disclosed in U.S. Pat. No. 4,536,516. Another related compound is 4-hydroxy tamoxifen which is disclosed in U.S. Pat. No. 4,623,660.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-,2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2,dimethyl-3-phenyl-chroman-4-yl)-phenoxy)-ethyl)-pyrrolidine, which is disclosed in U.S. Pat. No. 3,822,287. Also preferred is levormeloxifene. Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc. Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetr ahydro-naphthalene-2-ol; (−)-cis-6-phenyl-5-(4-(2-pyrrolidin-1-yl-ethoxy)-phenyl)-5,6,7,8-tetrahydro-naphthalene-2-ol; cis-6-phenyl-5-(4-(2-pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline. Other estrogen agonist/antagonists are described in U.S. Pat. No. 4,133,814. U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study, "Assessment of Fracture Risk and its Application to Screening for Postmenopausal Osteoporosis (1994). Report of a WHO Study Group. World Health Organization Technical Series 843." Any prostaglandin, or prostaglandin agonist/antagonist may be used in combination with the compounds of this invention. Those skilled in the art will recognize that IGF-1, sodium fluoride, parathyroid hormone (PTH), active fragments of parathyroid hormone, growth hormone or growth hormone secretagogues may also be used. The following paragraphs describes in greater detail exemplary compounds that may be administered in combination with compounds of this invention Prostaglandins: The term prostaglandin refers to compounds which are analogs of the natural prostaglandins $PGD_1$, $PGD_2$, $PGE_2$, $PGE_1$ and $PGF_2$ which are useful in the treatment of osteoporosis and other disorders associated with excessive osteoclastic bone resorption. These compounds bind to the prostaglandins receptors. Such binding is readily determined by those skilled in the art of standard assays (e.g., S. An et al., Cloning and Expression of the $EP_2$ Subtype of Human Receptors for Prostaglandin $E_2$ Biochemical and Biophysical Research Communications, 197(1): 263-270 (1993)).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$-$C_{14}$ and a cis double bond at the $C_5$-$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197. Norrdin et al., The Role of Prostaglandins in Bone in Vivo, Prostaglandins Leukotriene Essential Fatty Acids 41: 139-150 (1990) is a review of bone anabolic prostaglandins. Any prostaglandin agonist/antagonist may be used in combination with the compounds of this invention. The term prostaglandin agonist/antagonist refers to compounds which bind to prostaglandin receptors (e.g., An S. et al., Cloning and Expression of the $EP_2$ Subtype of Human Receptors for Prostaglandin $E_2$, Biochemical and Biophysical Research Communications 197(1): 263-70 (1993)) and mimic the action of prostaglandin in vivo (e.g., stimulate bone formation and increase bone mass). Such actions are readily determined by those skilled in the art of standard assays. Eriksen E. F. et al., Bone Histomorphometry, Raven Press, New York, 1994, pp. 1-74; S. J. Grier et al., The Use of Dual-Energy X-Ray Absorptiometry In Animals, Inv. Radiol. 31(1): 50-62 (1996); H. W. Wahner and I. Fogelman, The Evaluation of Osteoporosis: Dual Energy X-Ray Absorptiometry in Clinical Practice, Martin Dunitz Ltd. London, pp. 1-296 (1994). A number of these compounds are described and reference below. However, other prostaglandin agonists/antagonists will be known to those skilled in the art. Exemplary prostaglandin agonists/antagonists are disclosed as follows. U.S. Pat. No. 3,932,389 discloses 2-descarboxy-2-(tetrazol-5-yl)-11-desoxy-15-substituted-omega-pentanorpros taglandins useful for bone formation activity. U.S. Pat. No. 4,018,892, discloses 16-aryl-13,14-dihydro-$PGE_2$ p-biphenyl esters useful for bone formation activity. U.S. Pat. No. 4,219,483, discloses 2,3,6-substituted-4-pyrones useful for bone formation activity. U.S. Pat. No. 4,132,847, discloses 2,3,6-substituted-4-pyrones useful for bone formation activity. U.S. Pat. No. 4,000,309, discloses 16-aryl-13,14-dihydro-$PGE_2$ p-biphenyl esters useful for bone formation activity. U.S. Pat. No. 3,982,016, discloses 16-aryl-13,14-dihydro-$PGE_2$ p-biphenyl esters useful for bone formation activity. U.S. Pat. No. 4,621,100, discloses substituted cyclopentanes useful for bone formation activity. U.S. Pat. No. 5,216,183, discloses cyclopentanones useful for bone formation activity.

Sodium fluoride may be used in combination with the compounds of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478. The activity of sodium fluoride is readily determined by those skilled in the art of biological protocols.

Bone morphogenetic protein may be used in combination with the compounds of this invention (e.g., see Ono et al., Promotion of the Osteogenetic Activity of Recombinant Human Bone Morphogenetic Protein by Prostaglandin $E_1$, Bone 19(6): 581-588 (1996)).

Any parathyroid hormone (PTH) may be used in combination with the compound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication No. WO 94/01460). Such bone anabolic functional activity is readily determined by those skilled in the art of standard assays. A variety of these compounds are described and referenced below. However, other parathyroid hormone will be known to those skilled in the art. Exemplary parathyroid hormones are disclosed in the following references. "Human Parathyroid Peptide Treatment of Vertebral Osteoporosis", Osteoporosis Int., 3, (Supp 1): 199-203. "PTH 1-34 Treatment of Osteoporosis with Added Hormone Replacement Therapy: Biochemical, Kinetic and Histological Responses" Osteoporosis Int. 1: 162-170.

Any growth hormone or growth hormone secretagogue may be used in combination with the compounds of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art. In particular, a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide: MK-667. Other preferred growth hormone secretagogues include 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt; 2-amino-N-(1-(R)-benzyloxymethyl-2-(3a-(R)-(4-fluoro-benzyl)-2-methyl-3-oxo-2,3,3a,4, 6,7-hexahydro-pyrazolo[4,3-c]pyridin-5-yl)-2-oxo-ethyl) isobutyramide; 2-amino-N-(2-(3a-(R)-benzyl-3-oxo-2,3,3a, 4,6,7-hexahydro-pyrazolo[4,3-c]pyridin-5-yl)-1-(R)benzyloxymethyl-2-oxo-ethyl)isobutyramide; and 2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide.

The other therapeutic agent can be a steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout, in Goodman & Gilman's The Pharmacological Basis of Therapeutics* 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

For arthritis, inflammation-mediated bone loss and other disorders that have an inflammatory component, preferred conventional treatments for use in combination therapy with the compounds and compositions of this invention include (without limitation) naproxen sodium (Anaprox® and Anaprox® DS, Roche), flurbiprofen (Ansaid®; Pharmacia), diclofenac sodium+misoprostil (Arthrotec®, Searle), valdecoxib (Bextra®, Pharmacia), diclofenac potassium (Cataflam® and Voltaren®, Novartis), celecoxib (Celebrex®, Pharmacia), sulindac (Clinoril®, Merck), oxaprozin (Daypro®, Pharmacia), salsalate (Disalcid®, 3M), diflunisal (Dolobid®, Merck), naproxen sodium (EC Naprosyn®, Roche), piroxicam (Feldene®, Pfizer), indomethacin (Indocin® and Indocin SR®, Merck), etodolac (Lodine® and Lodine XL®, Wyeth), meloxicam (Mobic®, Boehringer Ingelheim), ibuprofen (Motrin®, Pharmacia), naproxen (Naprelan®, Elan), naproxen (Naprosyn®, Roche), ketoprofen (Orudis® and Oruvail®, Wyeth), nabumetone (Relafen®, SmithKline), tolmetin sodium (Tolectin®, McNeil), choline magnesium trisalicylate (Trilisate®, Purdue Fredrick), and rofecoxib (Vioxx®, Merck).

In any case, where pain in a component of the target disorder, the other therapeutic agent can be an analgesic. Useful analgesics include, but are not limited to, phenacetin, butacetin, acetaminophen, nefopam, acetoamidoquinone, and mixtures thereof.

For use against osteoporosis, Paget's disease and other disorders associated with bone deterioration, preferred conventional agents that mayu be used in combination with compounds and compositions of this invention include (without limitation) bisphosphonates (such as etidronate (Didronel®, Procter & Gamble), pamidronate (Aredia®, Novartis), and alendronate (Fosamax®, Merck)), tiludronate (Skelid®, Sanofi-Synthelabo, Inc.), risedronate (Actonel®, Procter & Gamble/Aventis), calcitonin (Miacalcin®), estrogens (Climara®, Estrace®, Estraderm®, Estratab®, Ogen®, Ortho-Est®, Vivelle®, Premarin®, and others) estrogens and progestins (Activella™, FemHrt®, Premphase®, Prempro®, and others), parathyroid hormone and portions thereof, such as teriparatide (Forteo®, Eli Lilly and Co.), selective estrogen receptor modulators (SERMs) (such as raloxifene (Evista®)) and treatments currently under investigation (such as other parathyroid hormones, sodium fluoride, vitamin D metabolites, and other bisphosphonates and selective estrogen receptor modulators).

6. Any method of the present invention can comprise administering an effective amount of a composition or pharmaceutical composition comprising at least one compound of this invention to a cell, tissue, organ, animal or patient in need of such modulation, treatment or therapy. Such a method can optionally further comprise co-administration or combination therapy for treating an IL-12 production related disorder, wherein the administering further comprises administering before, concurrently with, and/or after the compound of this invention, at least one additional active agent selected from a TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSATD), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonistm. Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

7. TNF antagonists suitable for compositions, combination therapy, co-administration, devices and/or methods of the present invention include, but are not limited to, anti-TNF antibodies (such as, Remicade (Infliximab) or Humira (adalimumab)) for example, or, antigen-binding fragments thereof, and receptor molecules which bind specifically to TNF (such as, for example, Enbrel (Etanercept)); compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

For clarifiation, a "tumor necrosis factor antibody," "TNF antibody," or fragment and the like decreases, blocks, inhibits, abrogates or interferes with TNF activity in vitro, in situ and/or preferably in vivo. For example, a suitable TNF human antibody of the present invention can bind TNF-α and includes anti-TNF antibodies, antigen-binding fragments thereof, and specified mutants or domains thereof that bind specifically to TNF-α. A suitable TNF antibody or fragment can also decrease block, abrogate, interfere, prevent and/or inhibit TNF DNA transcription, or prevent and/or inhibit TNF RNA or protein synthesis, TNF release, TNF receptor signaling, membrane TNF cleavage, TNF activity, TNF production and/or synthesis.

The foregoing and other useful combination therapies will be understood and appreciated by those of skill in the art. Potential advantages of such combination therapies include the ability to use less of each of the individual active ingredients to minimize toxic side effects, synergistic improvements in efficacy, improved ease of administration or use and/or reduced overall expense of compound preparation or formulation.

The biological activities of a compound of the invention can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium](Promega, Madison, Wis.).

A compound of the invention can also be evaluated by animal studies. For example, one of such studies involves the ability of a test compound to treat adjuvant arthritis (i.e., an IL-12 overproduction related disorder) in rats.

The compounds of the invention can be prepared by the synthetic routes disclosed herein or by the methods disclosed in U.S. Pat. No. 6,384,032, filed Jun. 15, 2000, U.S. Pat. No. 6,680,315, filed Nov. 30, 2001, U.S. Pat. No. 6,693,097, filed Nov. 30, 2001, U.S. Pat. No. 6,660,733, filed Jul. 10, 2002, U.S. patent application Ser. No. 10/305,039, filed Nov. 26, 2002, U.S. patent application Ser. No. 10/985,696, filed Nov. 10, 2004, U.S. Provisional Patent Application No. 60/585,124, filed Jul. 1, 2004, U.S. Provisional Patent Application No. 60/626,609, filed on Nov. 10, 2004, The entire teachings of the above listed patents and patent applications are incorporated herein by reference. For example, the compounds of the invention can be synthesized by the method disclosed in Scheme I or Scheme II.

In Scheme I, a trihalo-triazine, -pyrimidine or -pyridine (compound (a)) is contacted with ammonia or a compound containing a primary or secondary amine group (compound (b)) in a polar or non-polar solvent to displace a first halo group and yield a dihalo-triazine, -pyrimidine or -pyridine substituted with a substituted or unsubstituted amino group (compound (c)). Typically, compound (b) is added to a mixture of compound (a) in the solvent that has been cooled to about −78° C. to about 10° C. After addition of compound (b) the solvent is allowed to heat up to room temperature. Generally, the reaction takes from about 15 minutes to about 20 hours. A second halo group can be displaced on the triazine, pyrimidine or pyridine core by adding a strong base to a mixture of a compound having an alcohol, mercapto, primary or secondary amino group (compound (d)) and compound (c) in a polar aprotic solvent, such as ethers (e.g., tetrahydrofuran (THF), dioxane, and diethyl ether), dimethyl sulfoxide (DMSO), 1-methyl-2-pyrrolidinone (NMP), dimethyl formamide (DMF), and dimethyl acetamide (DMA), to form compound (e). Examples of strong bases include NaH, KH, sodium metal, potassium metal, alkyl lithium, aryl lithium and the like. In one embodiment, the mixture of compound (d) and compound (c) is cooled to about −78° C. to about 10° C. before addition of the base and allowed to warm up to room temperature after addition of the base. Typically, the reaction takes from between about 30 minutes to about 24 hours. The final halo group on the triazine, pyrimidine or pyridine core can be displaced with hydrazine or a substituted hydrazine by heating compound (e) in an aprotic solvent in the presence of hydrazine or a substituted hydrazine to form compound (f). Typically, the reaction is heated to about 50° C. to about 120° C. for about 30 minutes to about 4 hours. The cyclic hydrazone (compound (h)) is formed by combining in the presence of a catalytic amount of an acid a cyclic ketone (compound (g)) with compound (f) in a polar solvent, such as water, an alcohol (e.g., methanol, ethanol, propanol, etc.), an ether (e.g., diethyl ether, methyl propyl ether, dibutyl ether, t-butyl methyl ether, etc.), a cyclic ether (e.g., THF, dioxane, etc.), and combinations thereof. The acid can be an organic acid (e.g., acetic acid) or an inorganic acid (e.g., HCl, HBr, $H_2SO_4$, etc.) and the reaction is typically carried out at room temperature for a period of about 1 hour to about 24 hours.

Scheme II is a method of preparing triazine, pyrimidine or pyridine compounds of the invention that have a substituent that is attached to the triazine, pyrimidine or pyridine core via a carbon group. A methyl-dihydroxy-triazine, -pyrimidine or -pyridine (compound (i)) is heated with phosphoryl halide, such as phosphoryl chloride, to replace the hydroxyl groups with halo groups and form a methyl-dihalo-triazine, -pyrimidine or -pyridine (compound (j)). Typically, the reaction is carried out using a large excess of the phosphoryl halide compared to compound (i). In one embodiment, the phosphoryl halide is used as the solvent for the reaction. The reaction mixture is heated to about 50° C. to about 120° C. for about 1 hour to about 6 hours. Compound (j) can then be dissolved in a polar aprotic solvent, such as THF, dimethyl ether, dioxane, or combinations thereof, cooled to about −78° C. to about −10° C. then a strong base, such as an alkyl lithium or an aryl lithium, is added to the mixture to remove a benzylic proton. After about 15 minutes to about 1 hour, a substituted or unsubstituted cyclic ether or a substituted or unsubstituted cyclic thioether (compound (l)) is added to the mixture and the reaction is allowed to warm to room temperature and stir for about 2 hours to about 24 hours to form compound (m).

The reaction adding the hydrazine and the reaction adding the cyclic ketone are preformed in the same manner as described for Scheme I to form compound (n) and compound (o), respectively.

Scheme I: Method I for preparing compounds of the invention.

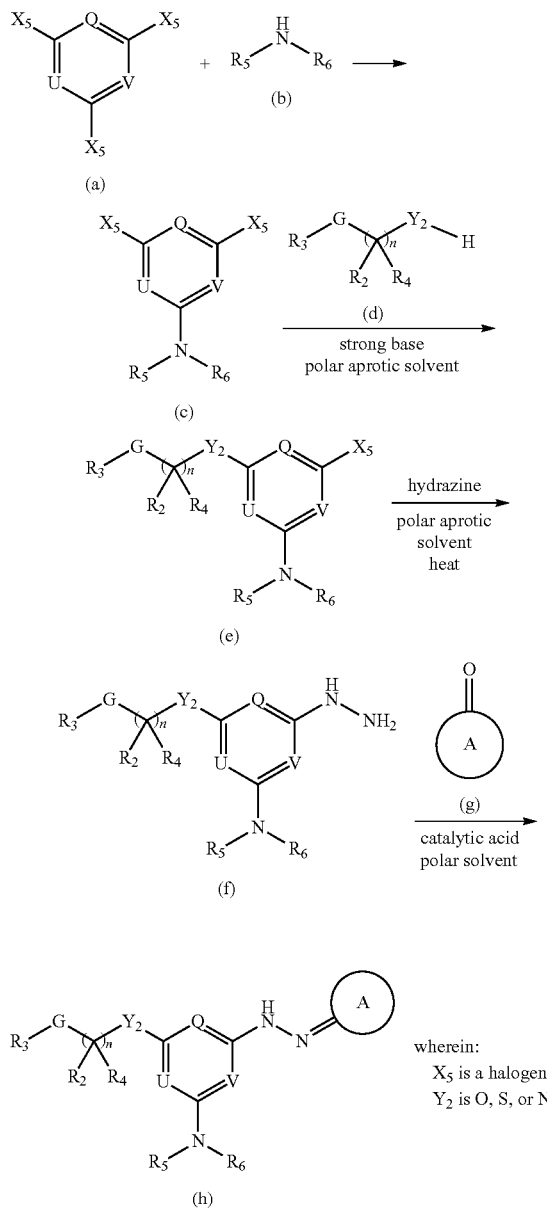

Scheme II: Method II for preparing compounds of the invention.

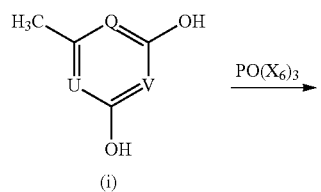

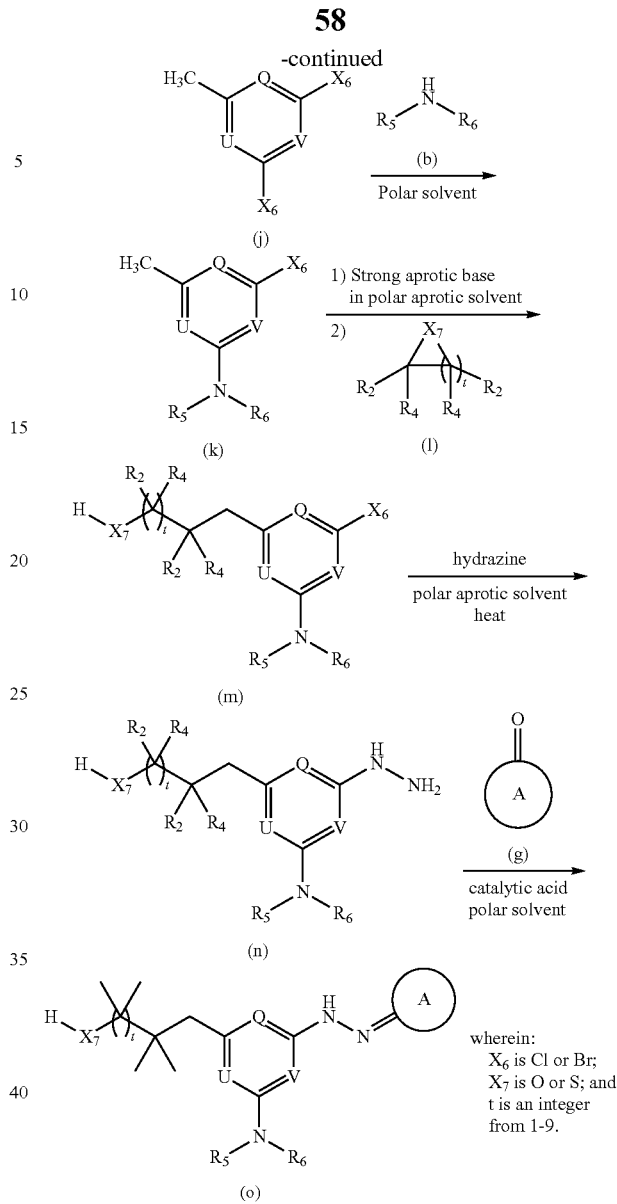

If preferred, other types of linkages can be prepared by similar reactions. Sensitive moieties on a triazine, pyrimidine, or pyridine intermediate and a nucleophile can be protected prior to coupling. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds of the invention. In addition, various synthetic steps may be performed in an alternate sequence or order to give the desired compounds. Synthetic chemistry transformations and protecting group methodologies (protection and deprotection) useful in synthesizing applicable compounds of the invention are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Correspondingly, pyridine, pyrimidine and triazine compounds described herein can be made according to methods know in the art, including those in the aforementioned treatises. It is recognized by one of ordinary skill that pyrimidines demonstrate reactivity intermediate relative to that of pyridines and triazines, therefore reaction conditions (e.g., temperature, reaction time, etc.) may be adjusted accordingly, which is routine for one of ordinary skill.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate). Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine). Bases are useful in either catalytic or stoichiometric amounts to facilitate chemical reactions.

Without further elaboration, it is believed that the above description has adequately enabled the present invention. The following specific embodiments are, therefore, to be construed as merely illustrative, and not limitative of the remainder of the disclosure in any way whatsoever. All of the references and publications cited herein are hereby incorporated by reference in their entirety.

EXAMPLES

Example 1

Synthesis of 5-methyl-3-{[6-morpholin-4-yl-2-(2-morpholin-4-yl-ethoxy)-pyrimidin-4-yl]-hydrazono}-1,3-dihydro-indol-2-one (Compound 1)

Step 1: Preparation of 6-Morpholino-2,4-dichloropyrimidine

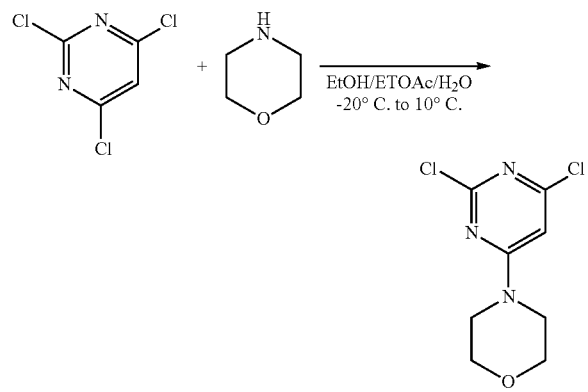

A 2-liter, 3-neck flask equipped with mechanical stirrer, thermometer and dropping funnel was loaded with ethanol (375 mL), water (375 mL) and morpholine, (1.01 mol, 88 g); the resulting solution was cooled (with sodium chloride-ice mixture) to about 0° C. and a solution of 2,4,6-trichloropyrimidine (91.17 g, 0.5 mol) in ethyl acetate (37.5 mL) was added dropwise in about 20 minutes, to maintain temperature below 10° C. The dropping funnel was rinsed twice with ethyl acetate (3 mL), and the rinses were transferred to the reaction mixture. The reaction was checked by TLC to determine when the reaction was complete. After completion of the reaction, ice water (375 mL) was added, and reaction was allowed to stir for 30 minutes to complete precipitation. The colorless solid was filtered out, washed 6 times with water (225 mL per wash) and vacuum-dried at 40-50° C. until a constant weight of the product was maintained. The product (114.7 g, 98% yield) was a mixture of regioisomers 6-morpholino-2,4-dichloropyrimidine and 2-morpholino-4,6-dichloropyrimidine in about a 3.9:1 ratio which were separated by chromatograph to 6-morpholino-2,4-dichloropyrimidine.

Step 2: Preparation of 4-[2-(4-Chloro-6-(morpholin-4-yl)-pyrimidin-2-yloxy)-ethyl]-morpholine

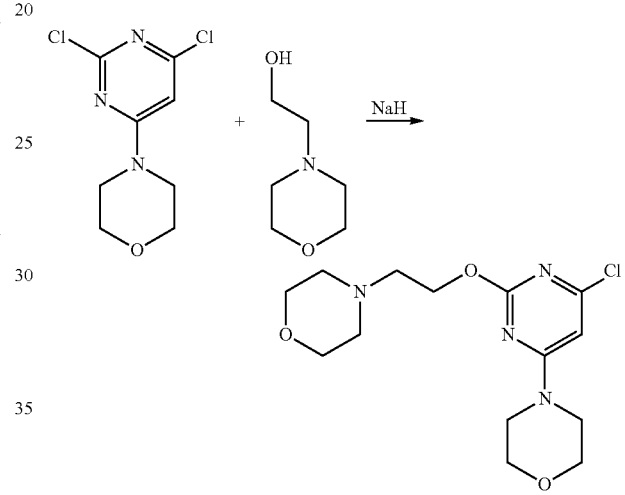

6-Morpholino-2,4-dichloropyrimidine (4.6 g; 20 mmol) and 4-(2-hydroxyethyl)-morpholine (3.3 g; 25 mmol) were dissolved in tetrahydrofuran (200 mL), and chilled in an ice bath. To the solution was added sodium hydride (600 mg; 25 mmol), and it was stirred overnight at room temperature. The solvents were evaporated, and the solid was dissolved in dichloromethane (200 mL) which was then washed with water (2×100 mL). The organic layer was dried over magnesium sulfate, evaporated, and purified by column chromatography to give 4-[2-(4-Chloro-6-(morpholin-4-yl)-pyrimidin-2-yloxy)-ethyl]-morpholine (4.5 g).

Step 3: Preparation of 4-[2-(4-hydrazino-6-(morpholin-4-yl)-pyrimidin-2-yloxy)-ethyl]-morpholine

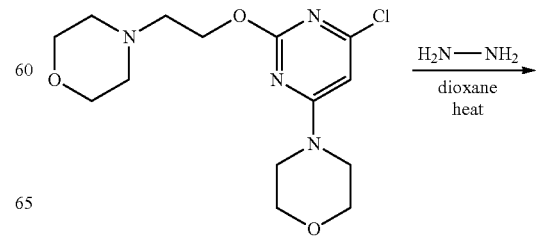

-continued

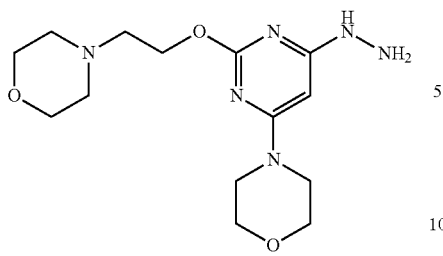

4-[2-(4-Chloro-6-(morpholin-4-yl)-pyrimidin-2-yloxy)-ethyl]-morpholine (2.0 g; 6 mmol) was dissolved in dioxane (100 mL) and hydrazine (2 mL; 60 mmol) was added. The solution was heated to reflux for one hour, at which point the solvent was evaporated. The solid was dissolved in dichloromethane (100 mL) and washed with 10% sodium carbonate (10 mL). The organic layer was dried over magnesium sulfate and evaporated to give 4-[2-(4-Hydrazino-6-(morpholin-4-yl)-pyrimidin-2-yloxy)-ethyl]-morpholine (2.0 g)

Step 4: Preparation of 5-methyl-3-{[6-morpholin-4-yl-2-(2-morpholin-4-yl-ethoxy)-pyrimidin-4-yl]-hydrazono}-1,3-dihydro-indol-2-one

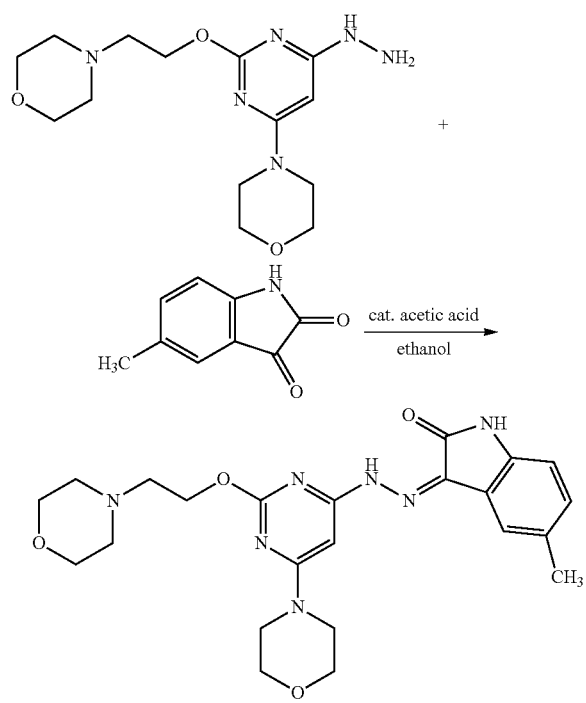

4-[2-(4-Hydrazino-6-(morpholin-4-yl)-pyrimidin-2-yloxy)-ethyl]-morpholine (80 mg; ¼ mmol) was added to a flask along with 5-methylisatin (53 mg; ⅓ mmol) and ethanol (4 mL). One drop of acetic acid was added, and the reaction was stirred overnight at 60° C. The mixture was then filtered and the precipitate was washed with ethanol (1 mL) and dried to give 5-methyl-3-{[6-morpholin-4-yl-2-(2-morpholin-4-yl-ethoxy)-pyrimidin-4-yl]-hydrazono}-1,3-dihydro-indol-2-one.

Example 2

Synthesis of N-(6-Methyl-chroman-4-ylidene)-N'-[6-morpholin-4-yl-2-(2-morpholin-4-yl-ethoxy)-pyrimidin-4-yl]-hydrazine (Compound 2)

Compound 2 was made in an analogous fashion to Compound 1 except that 6-methyl-chroman-4-one was used in step 4 of Example 1 instead of 5-methylisatin.

Example 3

Synthesis of N-(6-Methyl-indan-1-ylidene)-N'-[6-morpholin-4-yl-2-(2-morpholin-4-yl-ethoxy)-pyrimidin-4-yl]-hydrazine (Compound 3)

Compound 3 was made in an analogous fashion to Compound 1 except that 6-methyl-indan-1-one was used in step 4 of Example 1 instead of 5-methylisatin.

Example 4

Synthesis of N-(Indan-1-ylidene)-N'-[6-morpholin-4-yl-2-(2-morpholin-4-yl-ethoxy)-pyrimidin-4-yl]-hydrazine (Compound 4)

Compound 4 was made in an analogous fashion to Compound 1 except that indan-1-one was used in step 4 of Example 1 instead of 5-methylisatin.

Example 5

Synthesis of N-(Benzofuran-3-ylidene)-N'-[6-morpholin-4-yl-2-(2-morpholin-4-yl-ethoxy)-pyrimidin-4-yl]-hydrazine (Compound 5)

Compound 5 was made in an analogous fashion to Compound 1 except that benzofuran-3-one was used in step 4 of Example 1 instead of 5-methylisatin.

Example 6

Synthesis of N-(3-Methyl-indan-1-ylidene)-N'-[6-morpholin-4-yl-2-(2-morpholin-4-yl-ethoxy)pyrimidin-4-yl]-hydrazine (Compound 6)

Compound 6 was made in an analogous fashion to Compound 1 except that 3-methyl-indan-1-one was used in step 4 of Example 1 instead of 5-methylisatin.

Example 7

Synthesis of N-(4-Methyl-indan-1-ylidene)-N'-[6-morpholin-4-yl-2-(2-morpholin-4-yl-ethoxypyrimidin-4-yl]-hydrazine (Compound 7)

Compound 7 was made in an analogous fashion to Compound 1 except that 4-methyl-indan-1-one was used in step 4 of Example 1 instead of 5-methylisatin.

Example 8

Synthesis of N-(5-Methoxy-indan-1-ylidene)-N'-[6-morpholin-4-yl-2-(2-morpholin-4-yl-ethoxy)-pyrimidin-4-yl]-hydrazine (Compound 8)

Compound 8 was made in an analogous fashion to Compound 1 except that 5-methoxy-indan-1-one was used in step 4 of Example 1 instead of 5-methylisatin.

Example 9

Synthesis of N-(6-Methoxy-indan-1-ylidene)-N'-[6-morpholin-4-yl-2-(2-morpholin-4-yl-ethoxy)-pyrimidin-4-yl]-hydrazine (Compound 9)

Compound 9 was made in an analogous fashion to Compound 1 except that 6-methoxy-indan-1-one was used in step 4 of Example 1 instead of 5-methylisatin.

Example 10

Synthesis of N-(Indan-2-ylidene)-N'-[6-morpholin-4-yl-2-(2-morpholin-4-yl-ethoxy)-pyrimidin-4-yl]-hydrazine (Compound 10)

Compound 10 was made in an analogous fashion to Compound 1 except that indan-2-one was used in step 4 of Example 1 instead of 5-methylisatin.

Example 11

Synthesis of N-(3,4-Dihydro-2H-naphthalen-1-ylidene)-N'-[6-morpholin-4-yl-2-(2-morpholin-4-yl-ethoxy)-pyrimidin-4-yl]-hydrazine (Compound 11)

Compound 11 was made in an analogous fashion to Compound 1 except that tetralone was used in step 4 of Example 1 instead of 5-methylisatin.

Example 12

Synthesis of N-(Chroman-4-ylidene)-N'-[6-morpholin-4-yl-2-(2-morpholin-4-yl-ethoxy)-pyrimidin-4-yl]-hydrazine (Compound 12)

Compound 12 was made in an analogous fashion to Compound 1 except that chroman-4-one was used in step 4 of Example 1 instead of 5-methylisatin.

Example 13

Synthesis of N-(6-Methoxy-3,4-dihydro-2H-naphthalen-1-ylidene)-N'-[6-morpholin-4-yl-2-(2-morpholin-4-yl-ethoxy)-pyrimidin-4-yl]-hydrazine (Compound 13)

Compound 13 was made in an analogous fashion to Compound 1 except that 6-methoxy-tetralone was used in step 4 of Example 1 instead of 5-methylisatin.

Example 14

Synthesis of N-(7-Methoxy-3,4-dihydro-2H-naphthalen-1-ylidene)-N'-[6-morpholin-4-yl-2-(2-morpholin-4-yl-ethoxy)-pyrimidin-4-yl]-hydrazine (Compound 14)

Compound 14 was made in an analogous fashion to Compound 1 except that 7-methoxy-tetralone was used in step 4 of Example 1 instead of 5-methylisatin.

Example 15

Synthesis of N-(7-Nitro-3,4-dihydro-2H-naphthalen-1-ylidene)-N'-[6-morpholin-4-yl-2-(2-morpholin-4-yl-ethoxy)-pyrimidin-4-yl]-hydrazine (Compound 15)

Compound 15 was made in an analogous fashion to Compound 1 except that 7-nitro-tetralone was used in step 4 of Example 1 instead of 5-methylisatin.

Example 16

Synthesis of N-(6-Hydroxy-3,4-dihydro-2H-naphthalen-1-ylidene)-N'-[6-morpholin-4-yl-2-(2-morpholin-4-yl-ethoxy)-pyrimidin-4-yl]-hydrazine (Compound 16)

Compound 16 was made in an analogous fashion to Compound 1 except that 6-hydroxy-tetralone was used in step 4 of Example 1 instead of 5-methylisatin.

Example 17

Synthesis of N-(5,7-Dimethyl-3,4-dihydro-2H-naphthalen-1-ylidene)-N'-[6-morpholin-4-yl-2-(2-morpholin-4-yl-ethoxy)-pyrimidin-4-yl]-hydrazine (Compound 17)

Compound 17 was made in an analogous fashion to Compound 1 except that 5,7-dimethyl-tetralone was used in step 4 of Example 1 instead of 5-methylisatin.

Example 18

Synthesis of N-(6,7-Dimethoxy-3,4-dihydro-2H-naphthalen-1-ylidene)-N'-[6-morpholin-4-yl-2-(2-morpholin-4-yl-ethoxy)-pyrimidin-4-yl]-hydrazine (Compound 18)

Compound 18 was made in an analogous fashion to Compound 1 except that 6,7-dimethoxy-tetralone was used in step 4 of Example 1 instead of 5-methylisatin.

Example 19

Synthesis of N-(4-Methyl-3,4-dihydro-2H-naphthalen-1-ylidene)-N'-[6-morpholin-4-yl-2-(2-morpholin-4-yl-ethoxy)-pyrimidin-4-yl]-hydrazine (Compound 19)

Compound 19 was made in an analogous fashion to Compound 1 except that 4-methyl-tetralone was used in step 4 of Example 1 instead of 5-methylisatin.

Example 20

Synthesis of 1-Methyl-3-{[6-morpholin-4-yl-2-(2-morpholin-4-yl-ethoxy)-pyrimidin-4-yl]-hydrazono}-1,3-dihydro-indol-2-one (Compound 20)

Compound 20 was made in an analogous fashion to Compound 1 except that 1-methyl-1H-indol-2,3-dione was used in step 4 of Example 1 instead of 5-methylisatin.

Example 21

Synthesis of 3-(2-{4-[N'-(6-Methyl-indan-1-ylidene)-hydrazino]-6-morpholin-4-yl-pyrimidin-2-yloxy}-ethyl)-oxazolidin-2-one (Compound 21)

Step 1: Preparation of 3-(2-Hydroxy-ethyl)-oxazolidin-2-one

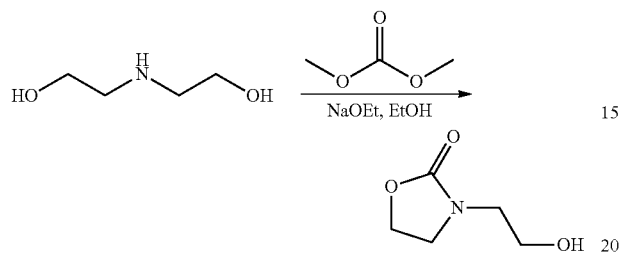

To a stirred solution of equimolar amount of 2-(2-hydroxyethylamino)-ethanol and dimethylcarbonate in ethanol (10 mL/g) was added 0.1 eqv. of sodium ethoxide. The mixture thus obtained was refluxed for 3 h and cooled. The mixture was concentrated, then dissolved in dichloromethane. It was then passed through a short pad of silica gel, washed with ethylacetate successively and concentrated to obtain 3-(2-hydroxy-ethyl)-oxazolidin-2-one as colorless oil. The product was used without further purification.

Step 2: Preparation of Compound 21

Compound 21 was made in an analogous fashion to Compound 1 except that 6-methyl-indan-1-one was used in step 4 of Example 1 instead of 5-methylisatin, and 3-(2-hydroxyethyl)-oxazolidin-2-one was used instead of 4-(2-hydroxyethyl)-morpholine in step 2 of Example 1.

Example 22

Synthesis of 3-(2-{4-[N'-(6-Hydroxy-3,4-dihydro-2H-naphthalen-1-ylidene)-hydrazino]-6-morpholin-4-yl-pyrimidin-2-yloxy}-ethyl)-oxazolidin-2-one (Compound 22)

Compound 22 was made in an analogous fashion to Compound 1 except that 6-hydroxy-tetralone was used in step 4 instead of 5-methylisatin, and 3-(2-hydroxy-ethyl)-oxazolidin-2-one was used instead of 4-(2-hydroxyethyl)-morpholine in step 2 of Example 1.

Example 23

Synthesis of 2-Methyl-4-{4-[N'-(6-methyl-indan-1-ylidene)-hydrazino]-6-morpholin-4-yl-pyrimidin-2-yloxy}-butan-2-ol (Compound 23)

Step 1: Preparation of 2-Methyl-4,6-dichloropyrimidine

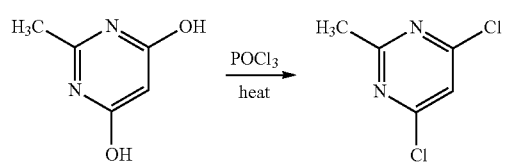

2-Methyl-4,6-dihydroxypyrimidine (42.0 g.; 333 mmol) was added to phosphoryl chloride (350 mL). The reaction mixture was heated at reflux for three hours. The solvent was removed under reduced pressure until the volume was approximately 100 mL, and the reaction mixture was then poured onto ice (500 mL) and stirred for ten minutes. Dichloromethane (200 mL) was added, and after shaking, the organic layer was dried with sodium sulfate and evaporated to yield crude 2-methyl-4,6-dichloropyrimidine (41.8 g.; 256 mmol).

Step 2: Preparation of 2-Methyl-4-chloro-6-morpholino-pyrimidine

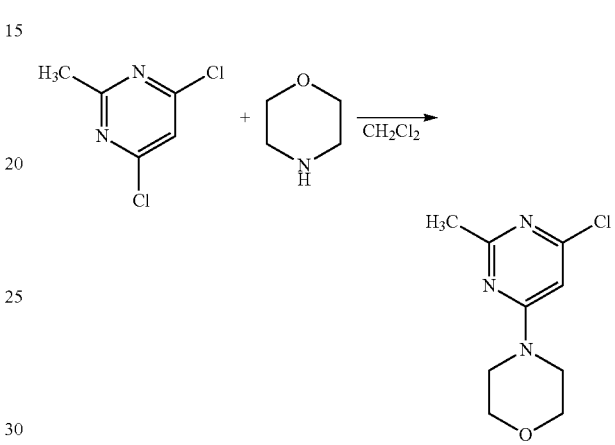

The crude 2-methyl-4,6-dichloropyrimidine (41.8 g.; 256 mmol) was dissolved in dichloromethane (200 mL) and chilled to −78° C. in an inert atmosphere. Morpholine (48 g.; 550 mol) dissolved in dichloromethane (100 mL) was added slowly. The reaction was allowed to warm to room temperature while stirring overnight. The organic layer was washed with saturated ammonium chloride (2×100 mL), dried with sodium sulfate, and evaporated to give 2-methyl-4-chloro-6-morpholino-pyrimidine (48.5 g.; 227 mmol).

Step 3: Preparation of 4-(4-Chloro-6-morpholin-4-yl-pyrimidin-2-yl)-2-methyl-butan-2-ol

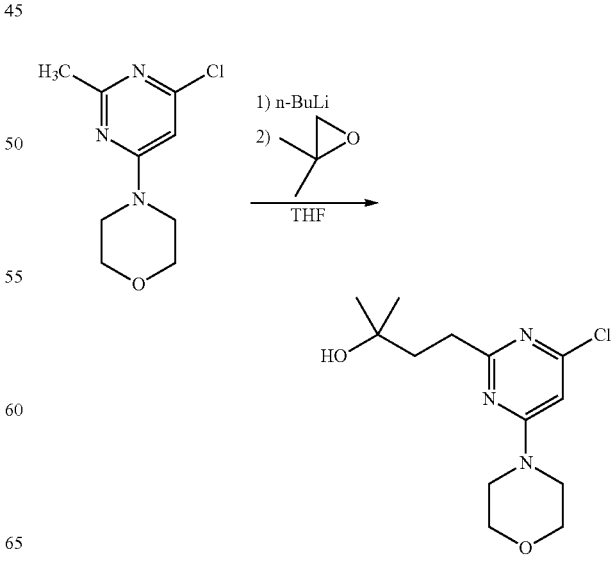

2-Methyl-4-chloro-6-morpholino-pyrimidine (10.7 g.; 50 mmol) was dissolved in tetrahydrofuran (200 mL). The reaction was chilled to −78° C. under an inert atmosphere. A solution of n-butyllithium in hexanes (25 mL, 2.5M, 62.50 mmol) was added, and the reaction mixture was stirred for thirty minutes. A solution of isobutylene oxide 6.6 mL, 75 mmol) was added, and the reaction was allowed to warm to room temperature while stirring overnight. The solvent was removed under reduced pressure, and the crude material was dissolved in methylene chloride (200 mL) and washed with saturated ammonium chloride (2×50 mL), dried with sodium sulfate, and evaporated to dryness. The compound was purified by column chromatography to give 4-(4-chloro-6-morpholin-4-yl-pyrimidin-2-yl)-2-methyl-butan-2-ol (6.2 g., 21.7 mmol).

Step 4: Preparation of 4-(4-Hydrazino-6-morpholin-4-yl-pyrimidin-2-yl)-2-methyl-butan-2-ol

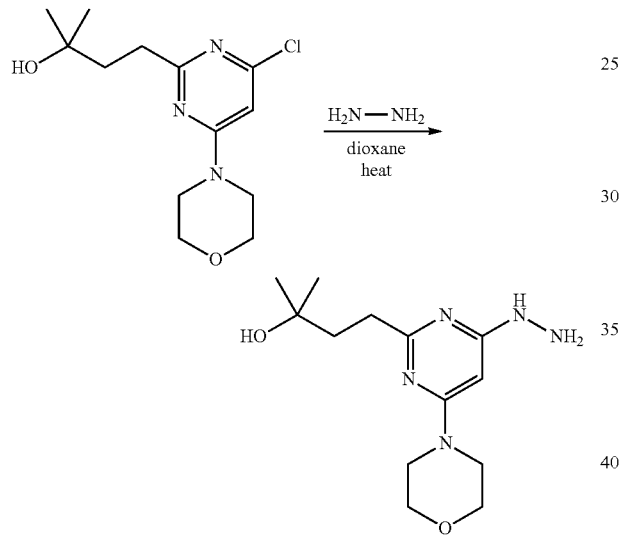

4-(4-chloro-6-morpholin-4-yl-pyrimidin-2-yl)-2-methyl-butan-2-ol (3.3 g., 11.5 mmol) was dissolved in dioxane (30 mL). To the reaction mixture was added anhydrous hydrazine (7.5 mL, 220 mmol). The reaction was then heated at reflux for five hours. The solvent was removed under reduced pressure, and the crude solid was dissolved in a mixture of dichloromethane (800 mL) and 10% potassium carbonate (40 mL). The organic layer was isolated, dried with sodium sulfate, and evaporated to give 4-(4-hydrazino-6-morpholin-4-yl-pyrimidin-2-yl)-2-methyl-butan-2-ol (2.61 g., 9.2 mmol).

Step 5: Preparation of 2-Methyl-1-{4-[N'-(6-methyl-indan-1-ylidene)-hydrazino]-6-morpholin-4-yl-pyrimidin-2-yloxy}-propan-2-ol (Compound 23)

Compound 23 was made in an analogous fashion to step 4 of Example 1 except that 4-(4-hydrazino-6-morpholin-4-yl-pyrimidin-2-yl)-2-methyl-butan-2-ol was used instead of 4-[2-(4-hydrazino-6-(morpholin-4-yl)-pyrimidin-2-yloxy)-ethyl]-morpholine, and 6-methyl-indan-1-one was used instead of 5-methylisatin.

Example 24

Synthesis of 5-{[2-(3-Hydroxy-3-methyl-butyl)-6-morpholin-4-yl-pyrimidin-4-yl]-hydrazono}-5,6,7,8-tetrahydro-naphthalen-2-ol (Compound 24)

Compound 24 was made in an analogous fashion to step 4 of Example 1 except that 4-(4-hydrazino-6-morpholin-4-yl-pyrimidin-2-yl)-2-methyl-butan-2-ol was used instead of 4-[2-(4-hydrazino-6-(morpholin-4-yl)-pyrimidin-2-yloxy)-ethyl]-morpholine, and 6-hydroxy-tetralone was used instead of 5-methylisatin.

Example 25

Synthesis of N-(4-Hydroxy-indan-1-ylidene)-N'-[6-morpholin-4-yl-2-(2-morpholin-4-yl-ethoxy)-pyrimidin-4-yl]-hydrazine (Compound 25)

Compound 25 was made in an analogous fashion to Compound 1 except that 4-hydroxy-indan-1-one was used in step 4 of Example 1 instead of 5-methylisatin.

Example 26

Synthesis of N-(5-Hydroxy-indan-1-ylidene)-N'-[6-morpholin-4-yl-2-(2-morpholin-4-yl-ethoxy)-pyrimidin-4-yl]-hydrazine (Compound 26)

Compound 26 was made in an analogous fashion to Compound 1 except that 5-hydroxy-indan-1-one was used in step 4 of Example 1 instead of 5-methylisatin.

Example 27

Synthesis of 3-{[6-Morpholin-4-yl-2-(2-morpholin-4-yl-ethoxy)-pyrimidin-4-yl]-hydrazono}-2,3-dihydro-benzofuran-6-ol (Compound 27)

Compound 27 was made in an analogous fashion to Compound 1 except that 6-hydroxy-benzofuran-3-one was used in step 4 of Example 1 instead of 5-methylisatin.

Example 28

Synthesis of N-(5-Hydroxy-3,4-dihydro-naphthalen-1-ylidene)-N'-[6-morpholin-4-yl-2-(2-morpholin-4-yl-ethoxy)-pyrimidin-4-yl]-hydrazine (Compound 28)

Compound 28 was made in an analogous fashion to Compound 1 except that 5-hydroxy-tetralone was used in step 4 of Example 1 instead of 5-methylisatin.

Example 29

Synthesis of N-(6-Fluoro-chroman-4-ylidene)-N'-[6-morpholin-4-yl-2-(2-morpholin-4-yl-ethoxy)-pyrimidin-4-yl]-hydrazine (Compound 29)

Compound 29 was made in an analogous fashion to Compound 1 except that 6-fluoro-chroman-4-one was used in step 4 of Example 1 instead of 5-methylisatin.

Example 30

Synthesis of N-(5-Fluoro-indan-1-ylidene)-N'-[6-morpholin-4-yl-2-(2-morpholin-4-yl-ethoxy)-pyrimidin-4-yl]-hydrazine (Compound 30)

Compound 30 was made in an analogous fashion to Compound 1 except that 5-fluoro-indan-1-one was used in step 4 of Example 1 instead of 5-methylisatin.

Example 31

Synthesis of N-(6,7-Dihydro-5H-benzo[1,2,5]oxadiazol-4-ylidene)-N'-[6-morpholin-4-yl-2-(2-morpholin-4-yl-ethoxy)-pyrimidin-4-yl]-hydrazine (Compound 31)

Compound 31 was made in an analogous fashion to Compound 1 except that 6,7-dihydro-5H-benzo[1,2,5]oxadiazol-4-one was used in step 4 of Example 1 instead of 5-methylisatin.

Example 32

Synthesis of N-[6-Morpholin-4-yl-2-(2-morpholin-4-yl-ethoxy)-pyrimidin-4-yl]-N'-(octahydro-naphthalen-1-ylidene)-hydrazine (Compound 32)

Compound 32 was made in an analogous fashion to Compound 1 except that octahydronaphthalen-1-one was used in step 4 of Example 1 instead of 5-methylisatin.

Example 33

Synthesis of N-(4-tert-Butyl-cyclohexylidene)-N'-[6-morpholin-4-yl-2-(2-morpholin-4-yl-ethoxy)-pyrimidin-4-yl]-hydrazine (Compound 33)

Compound 33 was made in an analogous fashion to Compound 1 except that A-tert-butyl-cyclohexanone was used in step 4 of Example 1 instead of 5-methylisatin.

Example 34

Synthesis of N-(2-Methyl-cyclohexylidene)-N'-[6-morpholin-4-yl-2-(2-morpholin-4-yl-ethoxy)-pyrimidin-4-yl]-hydrazine (Compound 34)

Compound 34 was made in an analogous fashion to Compound 1 except that 1-methyl-cyclohexanone was used in step 4 of Example 1 instead of 5-methylisatin.

Example 35

Synthesis of N-Cyclopentylidene-N'-[6-morpholin-4-yl-2-(2-morpholin-4-yl-ethoxy)-pyrimidin-4-yl]-hydrazine (Compound 35)

Compound 35 was made in an analogous fashion to Compound 1 except that cyclopentanone was used in step 4 of Example 1 instead of 5-methylisatin.

Example 36

Synthesis of N-Bicyclo[2.2.1]hept-2-ylidene-N'-[6-morpholin-4-yl-2-(2-morpholin-4-yl-ethoxy)-pyrimidin-4-yl]-hydrazine (Compound 36)

Compound 36 was made in an analogous fashion to Compound 1 except that bicycle[2.2.1]heptan-2-one was used in step 4 of Example 1 instead of 5-methylisatin.

Example 37

Synthesis of N-(6-Chloro-thiochroman-4-ylidene)-N'-[6-morpholin-4-yl-2-(2-morpholin-4-yl-ethoxy)-pyrimidin-4-yl]-hydrazine (Compound 37)

Compound 37 was made in an analogous fashion to Compound 1 except that 6-chloro-thiochroman-4-one was used in step 4 of Example 1 instead of 5-methylisatin.

Example 38

Synthesis of N-(6-Chloro-1,1-dioxo-1$\lambda^6$-thiochroman-4-ylidene)-N'-[6-morpholin-4-yl-2-(2-morpholin-4-yl-ethoxy)-pyrimidin-4-yl]-hydrazine (Compound 38)

Compound 38 was made in an analogous fashion to Compound 1 except that 6-chloro-1,1-dioxo-1$\lambda^6$-thiochroman-4-one was used in step 4 of Example 1 instead of 5-methylisatin.

Example 39

Synthesis of N-(6-Methyl-chromen-4-ylidene)-N'-[6-morpholin-4-yl-2-(2-morpholin-4-yl-ethoxy)-pyrimidin-4-yl]-hydrazine (Compound 39)

Compound 39 was made in an analogous fashion to Compound 1 except that 6-methyl-chromen-4-one was used in step 4 of Example 1 instead of 5-methylisatin.

Example 40

Synthesis of N-(6-Chloro-chromen-4-ylidene)-N'-[6-morpholin-4-yl-2-(2-morpholin-4-yl-ethoxy)-pyrimidin-4-yl]-hydrazine (Compound 40)

Compound 40 was made in an analogous fashion to Compound 1 except that 6-chloro-chromen-4-one was used in step 4 of Example 1 instead of 5-methylisatin.

Example 41

Synthesis of N-(6,7-Dihydro-5H-benzofuran-4-ylidene)-N'-[6-morpholin-4-yl-2-(morpholin-4-yl-ethoxy)-pyrimidin-4-yl]-hydrazine (Compound 41)

Compound 41 was made in an analogous fashion to Compound 1 except that 6,7-dihydro-5H-benzofuran-4-one was used in step 4 of Example 1 instead of 5-methylisatin.

Example 42

In Vitro Assays

8. Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFNγ were purchased from Boehringer Mannheim (Mannheim, Germany) and Pharmingen (San Diego, Calif.), respectively.

9. Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of $5 \times 10^5$ cells/well, and primed by adding IFNγ (30 U/mL) for 22 h and stimulated by adding LPS (1 μg/mL), or by adding IFNγ (100 U/mL) and then stimulated by adding SAC (0.01%). A test pyrimidine compound was dissolved in DMSO, and added to wells of the 96-well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the pyrimidine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

10. The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

11. Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with $1 \times 10^6$ cells/well. The splenocytes were then stimulated with a combination of IFNγ (60 ng/mL) and SAC (0.025%) [or LPS (20 μg/mL)] in the presence of a test compound. Cell-free supernatants were taken 24 h later for the measurement of cytokines. The preparation of compound and the assessment of cell viability were carried out as described above. Mouse IL-12 p70, IL-10, IL-ip, and TNFα were measured using ELISA kits from Endogen, according to the manufacturer's instructions.

The biological activities of compounds of the invention were tested on human PBMC or THP-1 cells. Representative $IC_{50}$ results for IL-12 are shown in Table 2.

TABLE 2

| Representative in vitro IC50 data | |
|---|---|
| $IC_{50}$ Range | Compounds |
| <1 μM | 1, 2, 3, 9, 13, 14, 15, 16, 17, 22, 23, 37, 39 |
| ≧1 μM | 4, 5, 6, 7, 8, 10, 11, 12, 19, 20, 24, 38, 41 |

Example 43

Treatment of Adjuvant Arthritis in Rats

Adjuvant arthritis (AA) was induced in female Lewis rats by the intracutaneous injection (base of the tail) of 0.1 mL of a 10 mg/mL bacterial suspension made from ground, heat-killed *Mycobacterium tuberculosis* H37Ra suspended in incomplete Freund's adjuvant. Rats were given a test compound orally once a day for 7 days (day 7-14), starting day 7 after mycobacterium induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws is thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index is 16.

Experiments with the AA model were repeated four times. Oral administration of compounds of this invention reproducibly reduced the arthritic score and delayed the development of polyarthritis in a dose-dependent manner. The percent reduction in arthritic score for animals treated with compounds of the invention is shown in Table 2. The arthritis score used in this model is a reflection of the inflammatory state of the structures monitored and the results therefore show the ability of the test compound to provide relief for this aspect of the pathology.

TABLE 2

The percent reduction in arthritic score for animals treated with compounds of the invention is shown.

| | Compound 2 | Compound 3 | Compound 9 |
|---|---|---|---|
| 20 mg/kg dose | 21% reduction | 25% reduction | 24% |
| 50 mg/kg dose | 32% reduction | No data | No data |

Example 44

Treatment of Crohn's Disease in Dinitrobenzene Sulfonic Acid-Induced Inflammatory Bowel Syndrome Model Rats Wistar derived male or female rats weighing 200±20 g and fasted for 24 hours are used. Distal colitis is induced by intra-colonic instillation of 2,4-dinitrobenzene sulfonic acid (DNBS, 25 mg in 0.5 mL ethanol 30%) after which air (2 mL) is gently injected through the cannula to ensure that the solution remained in the colon. A test compound and/or vehicle is administered orally 24 and 2 hours before DNBS instillation and then daily for 5 days. One control group is similarly treated with vehicle alone while the other is treated with vehicle plus DNBS. The animals are sacrificed 24 hours after the final dose of test compound administration and each colon is removed and weighed. Colon-to-body weight ratio is then calculated for each animal according to the formula: Colon (g)/BW×100. The "Net" increase in ratio of Vehicle-control+ DNBS group relative to Vehicle-control group is used as a base for comparison with test substance treated groups and expressed as "% Deduction."

Example 45

Treatment of Crohn's Disease in $CD4^+CD45Rb^{high}$ T Cell-Reconstituted SCID Colitis Model Mice Spleen cells are prepared from normal female BALB/c mice. For cell purification, the following anti-mouse antibodies are used to label non-CD4+ T cells: B220 (RA3-6B2), CD11b (M1/70), and CD8α (53-6.72). All antibodies are obtained from BioSource (Camarillo, Calif.). M450 anti-rat IgG-coated magnetic beads (Dynal, Oslo, Norway) are used to bind the antibodies and negative selection is accomplished using an MPC-1 magnetic concentrator. The enriched CD4+ cells are then labeled for cell sorting with FITC-conjugated CD45RB (16A, Pharmingen, San Diego, Calif.) and PE-conjugated CD4 (CT-CD4, Caltag, Burlingame, Calif.). CD4+ CD45RB$^{high}$ cells are operationally defined as the upper 40% of CD45Rb-staining CD4+ cells and sorted under sterile conditions by flow cytometry. Harvested cells are resuspended at $4\times10^6$/mL in PBS and injected 100 μL intraperitoneally into female C.B-17 SCID mice. Compounds of this invention and/or vehicle is orally administered once a day, 5 days per week, starting the day following the transfer. The transplanted SCID mice are weighed weekly and their clinical condition was monitored.

Colon tissue samples are fixed in 10% buffered formalin and embedded in paraffin. Sections (4 μm) collected from ascending, transverse, and descending colon are cut and stained with hematoxylin and eosin. The severity of colitis is determined based on histological examination of the distal colon sections, whereby the extent of colonic inflammation is graded on a scale of 0-3 in each of four criteria: crypt elongation, cell infiltration, depletion of goblet cells, and the number of crypt abscesses.

LP lymphocytes are isolated from freshly obtained colonic specimens. After removal of payer's patches, the colon is washed in Ca/Mg-free HBSS, cut into 0.5 cm pieces and incubated twice in HBSS containing EDTA (0.75 mM), DTT (1 mM), and antibiotics (amphotericin 2.5 μg/mL, gentamicin 50 μg/mL from Sigma) at 37° C. for 15 min. Next, the tissue is digested further in RPMI containing 0.5 mg/mL collagenase D, 0.01 mg/mL DNase I (Boehringer Manheim), and antibiotics at 37° C. LP cells are then layered on a 40-100% Percoll gradient (Pharmacia, Uppsala, Sweden), and lymphocyte-enriched populations are isolated from the cells at the 40-100% interface.

To measure cytokine production, 48-well plates are coated with 10 μg/mL murine anti-CD3ε antibody (145-2C11) in carbonate buffer (PH 9.6) overnight at 4° C. $5\times10^5$ LP cells are then cultured in 0.5 ml of complete medium in precoated wells in the presence of 1 μg/mL soluble anti-CD28 antibody (37.51). Purified antibodies are obtained from Pharmingen. Culture supernatants are removed after 48 h and assayed for cytokine production. Murine IFNγ is measured using an ELISA kit from Endogen (Cambridge, Mass.), according to the manufacturer's instructions.

Example 46

Inhibition of Osteoclast Formation

Human peripheral blood mononuclear cells (PBMC) are isolated from healthy donor blood. The cells are seeded in multi-well plates at $7.5\times10^5$ cells/ml in RPMI 1640 medium including 10% FBS. Osteoclast formation is induced with 20 ng/ml of recombinant human receptor activator of NF-kB-ligand (RANKL) and 10 ng/ml of human M-CSF in the presence of various doses of test compounds. After 48 hours of culture, RANKL and M-CSF is replenished and further cultured for 2 days. Then, the cultured cells are stained for tartrate-resistant acid phosphatase (TRAP). Osteoclasts are identified as TRAP-positive cells with more than 3 nuclei.

Total cell viability is assessed by CCK-8 assay (Dojindo, Gaithersburg, Md) with 24 hour incubation.

Other Embodiments

From the above description, one skilled in the art can easily ascertain the essential characteristics of the present invention, and without departing from the spirit and scope thereof, can make various changes and modifications of the invention to adapt it to various usages and conditions. For example, compounds structurally analogous to a heterocyclic compound described in the specification also can be made, screened for their inhibiting IL-12 activities, and used to practice this invention. Thus, other embodiments are also within the claims.

What is claimed:

1. A method of treating a subject with an IL-10 and/or IL-12 related disorder selected from the group consisting of adjuvant arthritis, inflammatory bowel disease, and Crohn's disease, said method comprising administering a compound represented by formula (II):

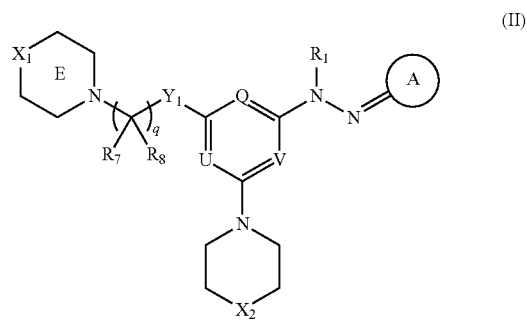

or a pharmaceutically acceptable salt thereof, wherein:

ring A is a ring system selected from the group consisting of:

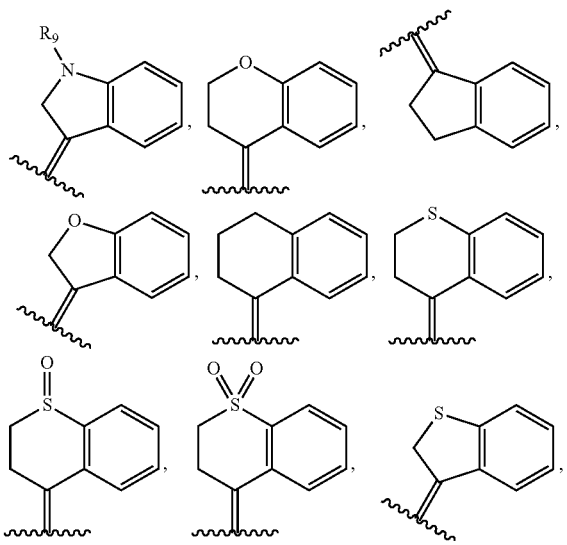

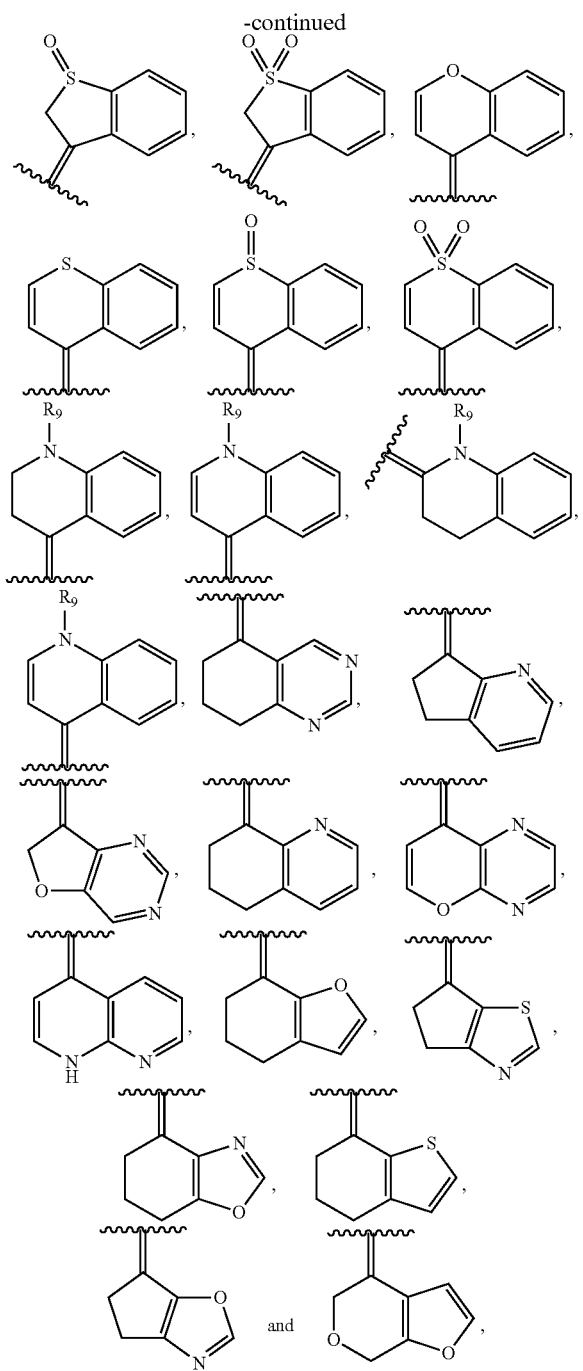

wherein:

" $\xi$ "

represents the point of attachment; and each ring system is optionally substituted with one or more substituents;

R₁, for each occurrence, is independently, H or a lower alkyl;

R$^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxyalkyl, alkylcarbonylalkyl, mercaptoalkyl, aminoalkyl, sulfonylalkyl, sulfonylaryl, or mercaptoalkoxy;

R$^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxyalkyl, alkylcarbonylalkyl, mercaptoalkyl, aminoalkyl, sulfonylalkyl, sulfonylaryl, mercaptoalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)₂R$^c$, —S(O)R$^c$, —NR$^k$S(O)₂R$^c$, —OS(O)₂R$^c$, —OP(O)R$^c$R$^c$, —P(O)R$^c$R$^c$, halo, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the nitrogen to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

ring E is optionally substituted with one to four substituents selected from a lower alkyl, a halo, an amino, a lower alkyl amino, a lower dialkyl amino, a cyano, a nitro, a lower haloalkyl, a hydroxyl, and a lower hydroxyalkyl;

V is CR$^g$, Q and U are N;

X₁ is O;

X₂ is O;

Y₁ is O;

R₇ and R₈, for each occurrence, are independently, H or a lower alkyl;

R₉ is H, an alkyl, an aralkyl, or an alkylcarbonyl; and q is 0, 1, 2, or 3.

2. The method of claim 1, wherein ring A is optionally substituted with from one to three substituents selected from the group consisting of a lower alkyl, a lower alkoxy, =O, nitro, cyano, hydroxy, amino, lower alkyl amino, lower dialkyl amino, mercapto, lower alkyl sulfanyl, halo, and haloalkyl.

3. A method of treating a subject with an IL-10 and/or IL-12 related disorder wherein the disorder is selected from the group consisting of adjuvant arthritis, inflammatory bowel disease, and Crohn's disease, comprising administering an effective amount of a compound selected from the group consisting of:

5-Methyl-3-{[6-morpholin-4-yl-2-(2-morpholin-4-yl-ethoxy)-pyrimidin-4-yl]-hydrazono}-1,3-dihydro-indol-2-one;

N-(6-Methyl-chroman-4-ylidene)-N'-[6-morpholin-4-yl-2-(2-morpholin-4-yl-ethoxy)-pyrimidin-4-yl]-hydrazine;

N-(6-Methyl-indan-1-ylidene)-N'-[6-morpholin-4-yl-2-(2-morpholin-4-yl-ethoxy)-pyrimidin-4-yl]-hydrazine;

N-(Indan-1-ylidene)-N'-[6-morpholin-4-yl-2-(2-morpholin-4-yl-ethoxy)-pyrimidin-4-yl]-hydrazine;

N-(Benzofuran-3-ylidene)-N'-[6-morpholin-4-yl-2-(2-morpholin-4-yl-ethoxy)-pyrimidin-4-yl]-hydrazine;

N-(3-Methyl-indan-1-ylidene)-N'-[6-morpholin-4-yl-2-(2-morpholin-4-yl-ethoxy)-pyrimidin-4-yl]-hydrazine;

N-(4-Methyl-indan-1-ylidene)-N'-[6-morpholin-4-yl-2-(2-morpholin-4-yl-ethoxy)-pyrimidin-4-yl]-hydrazine;

N-(5-Methoxy-indan-1-ylidene)-N'-[6-morpholin-4-yl-2-(2-morpholin-4-yl-ethoxy)-pyrimidin-4-yl]-hydrazine;

N-(6-Methoxy-indan-1-ylidene)-N'-[6-morpholin-4-yl-2-(2-morpholin-4-yl-ethoxy)-pyrimidin-4-yl]-hydrazine;

N-(Indan-2-ylidene)-N'-[6-morpholin-4-yl-2-(2-morpholin-4-yl-ethoxy)-pyrimidin-4-yl]-hydrazine;

N-(3,4-Dihydro-2H-naphthalen-1-ylidene)-N'-[6-morpholin-4-yl-2-(2-morpholin-4-yl-ethoxy)-pyrimidin-4-yl]-hydrazine;

N-(Chroman-4-ylidene)-N'-[6-morpholin-4-yl-2-(2-morpholin-4-yl-ethoxy)-pyrimidin-4-yl]-hydrazine;

N-(6-Methoxy-3,4-dihydro-2H-naphthalen-1-ylidene)-N'-[6-morpholin-4-yl-2-(2-morpholin-4-yl-ethoxy)-pyrimidin-4-yl]-hydrazine;

N-(7-Methoxy-3,4-dihydro-2H-naphthalen-1-ylidene)-N'-[6-morpholin-4-yl-2-(2-morpholin-4-yl-ethoxy)-pyrimidin-4-yl]-hydrazine;

N-(7-Nitro-3,4-dihydro-2H-naphthalen-1-ylidene)-N'-[6-morpholin-4-yl-2-(2-morpholin-4-yl-ethoxy)-pyrimidin-4-yl]-hydrazine;

N-(6-Hydroxy-3,4-dihydro-2H-naphthalen-1-ylidene)-N'-[6-morpholin-4-yl-2-(2-morpholin-4-yl-ethoxy)-pyrimidin-4-yl]-hydrazine;

N-(5,7-Dimethyl-3,4-dihydro-2H-naphthalen-1-ylidene)-N'-[6-morpholin-4-yl-2-(2-morpholin-4-yl-ethoxy)-pyrimidin-4-yl]-hydrazine;

N-(6,7-Dimethoxy-3,4-dihydro-2H-naphthalen-1-ylidene)-N'-[6-morpholin-4-yl-2-(2-morpholin-4-yl-ethoxy)-pyrimidin-4-yl]-hydrazine;

N-(4-Methyl-3,4-dihydro-2H-naphthalen-1-ylidene)-N'-[6-morpholin-4-yl-2-(2-morpholin-4-yl-ethoxy)-pyrimidin-4-yl]-hydrazine;

1-Methyl-3-{[6-morpholin-4-yl-2-(2-morpholin-4-yl-ethoxy)-pyrimidin-4-yl]-hydrazono}-1,3-dihydro-indol-2-one;

N-(4-Hydroxy-indan-1-ylidene)-N'-[6-morpholin-4-yl-2-(2-morpholin-4-yl-ethoxy)-pyrimidin-4-yl]-hydrazine;

N-(5-Hydroxy-indan-1-ylidene)-N'-[6-morpholin-4-yl-2-(2-morpholin-4-yl-ethoxy)-pyrimidin-4-yl]-hydrazine;

3-{[6-Morpholin-4-yl-2-(2-morpholin-4-yl-ethoxy)-pyrimidin-4-yl]-hydrazono}-2,3-dihydro-benzofuran-6-ol;

N-(5-Hydroxy-3,4-dihydro-naphthalen-1-ylidene)-N'-[6-morpholin-4-yl-2-(2-morpholin-4-yl-ethoxy)-pyrimidin-4-yl]-hydrazine;

N-(6-Fluoro-Chroman-4-ylidene)-N'-[6-morpholin-4-yl-2-(2-morpholin-4-yl-ethoxy)-pyrimidin-4-yl]-hydrazine, N-(5-Fluoro-indan-1-ylidene)-N'-[6-morpholin-4-yl-2-(2-morpholin-4-yl-ethoxy)-pyrimidin-4-yl]-hydrazine;

N-(6,7-Dihydro-5H-benzo[1,2,5]oxadiazol-4-ylidene)-N'-[6-morpholin-4-yl-2-(2-morpholin-4-yl-ethoxy)-pyrimidin-4-yl]-hydrazine;

N-[6-Morpholin-4-yl-2-(2-morpholin-4-yl-ethoxy)-pyrimidin-4-yl]-N'-(octahydro-naphthalen-1-ylidene)-hydrazine;

N-(4-tert-Butyl-cyclohexylidene)-N'-[6-morpholin-4-yl-2-(2-morpholin-4-yl-ethoxy)-pyrimidin-4-yl]-hydrazine;

N-(2-Methyl-cyclohexylidene)-N'-[6-morpholin-4-yl-2-(2-morpholin-4-yl-ethoxy)-pyrimidin-4-yl]-hydrazine;

N-Cyclopentylidene-N'-[6-morpholin-4-yl-2-(2-morpholin-4-yl-ethoxy)-pyrimidin-4-yl]-hydrazine;

N-Bicyclo[2.2.1]hept-2-ylidene-N'-[6-morpholin-4-yl-2-(2-morpholin-4-yl-ethoxy)-pyrimidin-4-yl]-hydrazine, N-(6-Chloro-thiochroman-4-ylidene)-N'-[6-morpholin-4-yl-2-(2-morpholin-4-yl-ethoxy)-pyrimidin-4-yl]-hydrazine;

N-(6-Chloro-1,1-dioxo-1$\lambda^6$-thiochroman-4-ylidene)-N'-[6-morpholin-4-yl-2-(2-morpholin-4-yl-ethoxy)-pyrimidin-4-yl]-hydrazine;

N-(6-Methyl-Chromen-4-ylidene)-N'-[6-morpholin-4-yl-2-(2-morpholin-4-yl-ethoxy)-pyrimidin-4-yl]-hydrazine;

N-(6-Chloro-chromen-4-ylidene)-N'-[6-morpholin-4-yl-2-(2-morpholin-4-yl-ethoxy)-pyrimidin-4-yl]-hydrazine; and N-(6,7-Dihydro-5H-benzofuran-4-ylidene)-N'-[6-morpholin-4-yl-2-(morpholin-4-yl-ethoxy)-pyrimidin-4-yl]-hydrazine;

or a pharmaceutically acceptable salt thereof.

\* \* \* \* \*